(12) United States Patent
Caprioli

(10) Patent No.: US 8,304,196 B2
(45) Date of Patent: *Nov. 6, 2012

(54) IN SITU ANALYSIS OF TISSUES

(75) Inventor: Richard Caprioli, Brentwood, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/942,840

(22) Filed: Nov. 9, 2010

(65) Prior Publication Data

US 2011/0190145 A1 Aug. 4, 2011

Related U.S. Application Data

(63) Continuation of application No. 11/355,912, filed on Feb. 16, 2006, now Pat. No. 7,829,291.

(60) Provisional application No. 60/653,665, filed on Feb. 17, 2005.

(51) Int. Cl.
*G01N 33/53* (2006.01)

(52) U.S. Cl. .......................................... 435/7.1; 436/518

(58) Field of Classification Search ........................ None
See application file for complete search history.

(56) References Cited

U.S. PATENT DOCUMENTS

| | | | | |
|---|---|---|---|---|
| 4,932,412 A | 6/1990 | Goldenberg | | 600/431 |
| 5,384,260 A * | 1/1995 | Osborne et al. | | 436/64 |
| 6,677,503 B1 | 1/2004 | Bidney et al. | | 800/279 |
| 6,707,038 B2 | 3/2004 | Ellson et al. | | 250/288 |
| 6,809,315 B2 | 10/2004 | Ellson et al. | | 250/288 |
| 7,534,338 B2 | 5/2009 | Hafeman et al. | | 205/288 |
| 2003/0049701 A1 * | 3/2003 | Muraca | | 435/7.23 |
| 2003/0186287 A1 | 10/2003 | Lin et al. | | 435/6 |
| 2004/0007673 A1 * | 1/2004 | Coon et al. | | 250/424 |
| 2007/0082356 A1 | 4/2007 | Strom et al. | | 435/6 |

FOREIGN PATENT DOCUMENTS

| | | |
|---|---|---|
| WO | WO 01/26460 | 4/2001 |
| WO | WO 03/034024 | 4/2003 |

OTHER PUBLICATIONS

Schwartz et al. (J. Mass Spectrometry 2003 vol. 38, p. 699-708).*
Pauletti et al. (J. Clin. Oncology 2000 vol. 18, 3651-3664).*
Office Action issued in U.S. Appl. No. 11/355,912, mailed Apr. 3, 2008.
Office Action issued in U.S. Appl. No. 11/355,912, mailed Dec. 8, 2009.
Office Action issued in U.S. Appl. No. 11/355,912, mailed May 22, 2009.
Yanagisawa et al., "Proteomic patterns of tumour subsets in non-small-cell lung cancer," *The Lancet*, 362:433-439, 2003.

* cited by examiner

*Primary Examiner* — Jacob Cheu
(74) *Attorney, Agent, or Firm* — Parker Highlander PLLC

(57) ABSTRACT

The present invention provides for the simultaneous assessment of a plurality of tissue regions or microregions, the benefit being homogeneity of the sampling, both in terms of tissue content and timing. Discrete regions of a tissue sample, such as those demarcated by microwells formed within the tissue itself or tissue plugs removed from the tissue in a spatially referenced fashion, can be treated with one or more physical or chemical treatments to liberate target molecules of interest. Subsequent analysis of said target molecules by, e.g., mass spectroscopy, permits identification of a variety of biological parameters, including those associated with disease or therapy.

8 Claims, 20 Drawing Sheets

IN SITU ANALYSIS OF TISSUES

This application is a Continuation Application of U.S. patent application Ser. No. 11/355,912 filed Feb. 16, 2006, now U.S. Pat. No. 7,829,291 which claims benefit of priority to U.S. Provisional Application Ser. No. 60/653,665, filed Feb. 17, 2005, the entire contents of both applications are hereby incorporated by reference in their entirety.

BACKGROUND OF THE INVENTION

1. Field of the Invention

The present invention relates generally to the fields of molecular biology. More particularly, it concerns measurement of biological molecules in situ in a tissue sample. Specifically, the invention provides for creation of a series of microwells in a single tissue or tissue region, thereby permitting analysis of proteins, nucleic acids, lipids, carbohydrates, drugs and other biomolecules in a homogeneous set of reactions.

2. Description of Related Art

With the completion of the Human Genome Project, emphasis is shifting to examining the protein complement of the human organism. This has given rise to the science of proteomics, the study of all the proteins produced by cell type and organism. At the same time, there has been a revival of interest in proteomics in many prokaryotes and lower eukaryotes as well.

The term proteome refers to all the proteins expressed by a genome, and thus proteomics involves the identification of proteins in the body and the determination of their role in physiological and pathophysiological functions. The ~30,000 genes defined by the Human Genome Project translate into 300,000 to 1 million proteins when alternate splicing and post-translational modifications are considered. While a genome remains unchanged to a large extent, the proteins in any particular cell change dramatically as genes are turned on and off in response to their environment.

As a reflection of the dynamic nature of the proteome, some researchers prefer to use the term "functional proteome" to describe all the proteins produced by a specific cell in a single time frame. Ultimately, it is believed that through proteomics, new disease markers and drug targets can be identified. Proteomics also has much promise in novel drug discovery via the analysis of clinically relevant molecular events. The future of biotechnology and medicine will be impacted greatly by proteomics, but advances are needed to realize the potential benefits.

With the availability of DNA microarray analysis, permitting the expression of thousands of genes to be monitored simultaneously, the importance of the proteome cannot be overstated as it is the proteins within the cell that provide structure, produce energy, and allow communication, movement and reproduction. Basically, proteins provide the structural and functional framework for cellular life.

However, there are several impediments in the study of proteins that are not inherent in the study of nucleic acids. Proteins are more difficult to work with than DNA and RNA. Proteins cannot be amplified like DNA, and are therefore less abundant sequences are more difficult to detect. Some proteins are difficult to analyze due to their poor solubility. And unlike DNA, the protein content of a given cell may vary depending on local conditions, even with a single organism or organ.

SUMMARY OF THE INVENTION

Therefore, in accordance with the present invention, there is provided a method for analyzing protein content in a tissue comprising (a) providing an intact tissue comprising a first spatially discrete microregion; (b) subjecting the microregion to one or more physical or chemical treatments; and (c) analyzing a protein sample from the microregion, thereby providing analysis of protein content in the tissue. The intact tissue may further comprise at least a second spatially discrete microregion, and the method further comprises subjecting the second spatially discrete microregion to one or more physical or chemical treatments, and analyzing discrete a protein sample from the second spatially discrete microregion, and the protein content of the first and second spatially discrete microregions may be compared. Protein encompasses both peptides and polypeptides. One or more of the steps may be automated.

The provision of a microregion may involve different aspects. In one embodiment, the microregion may comprise a well in a larger tissue section. The well may be a true depression or hole in the tissue, or a channel structure created in the tissue. Multiple wells, depressions or holes can be created in a spatially distinct manner. Alternatively, the intact tissue may be extracted from a larger tissue section, i.e., a tissue plug. The plug may then be transferred to a support for further treatment and analysis, and may be placed adjacent to other plugs in a spatially distinct manner to maintain the same or a pre-determined relationship to larger tissue section(s) from which they were extracted.

The tissue may be animal tissue, for example, heart tissue, liver tissue, kidney tissue, prostate tissue, breast tissue, ovary tissue, uterine tissue, skin tissue, lung tissue, brain tissue, colon tissue, head & neck tissue, pancreatic tissue, muscle tissue or skin or tissue that contains body fluids or contains traces of such fluids, such as blood, CSF, urine, saliva, mammary fluid. The animal tissue may be is diseased or injured, such as cancerous, inflamed, infected, congenitally diseased, functionally compromised (diabetes, neurodegenerative, or atrophy), traumatized or environmentally insulted. The tissue may be plant tissue, such as leaf tissue, stalk tissue, stem tissue, root tissue, or seed tissue. The plant tissue may be diseased or injured, such as tissue that is infected, congenitally diseased, traumatized or environmentally insulted.

The one or more physical or chemical treatments may comprise solvent treatment, detergent treatment, lipase treatment, proteolysis, reactive agent treatment or labeling. Labeling may comprise treatment with an isotope dilution reagent, a labeled antibody, or an enzyme. The analyzing may comprise secondary ion mass spectrometry, laser desorption mass spectrometry or matrix-assisted laser desorption mass spectrometry, desorption electrospray or electrospray mass spectrometry. Step (c) may be performed in situ in the microregion, or after removing the protein sample from the microregion.

The first and second spatially discrete microregions may receive distinct physical or chemical treatments or the same physical or chemical treatment. The first spatially discrete microregion or tissue adjacent to the first spatially microregion may be subject to a first test condition prior to step (b), such as a drug treatment, a nutrient treatment, a hormone treatment, an enzyme treatment, or a cytokine treatment. The method may further comprise subjecting the first spatially discrete microregion or tissue adjacent to a the first spatially discrete microregion to a second test condition prior to step (b). The second test condition may be different from the first test condition or the same as the first test condition. The first spatially discrete microregion is subjected to at least a second physical or chemical treatment, which may be distinct from the first treatment.

The microregion may be a microwell in the tissue, such as between 5 and 200 microns, between 10 and 100 microns, or about 50 microns. The microregion also may be is a tissue cylinder or plug. The method may further comprise generating the microregion, or a plurality of microregions, or a microregion array. The intact tissue may comprise 6 microregions, 24 microregions, or 96 microregions.

In accordance with any of the foregoing embodiments, the present invention may be modified to examine nucleic acids, lipids, carbohydrates, drugs, metabolites (endogenous and exogenous), xenobiotics, or any other biological molecule.

In another embodiment, there is provided a method for analyzing the delivery of an exogenous agent to a tissue comprising (a) providing an intact tissue comprising a first spatially discrete microregion; (b) contacting the tissue with the agent; (c) subjecting at the first spatially discrete microregion to one or more physical or chemical treatments; and (d) analyzing a sample from the first spatially discrete microregion, thereby providing analysis of the delivery of the exogenous agent to the tissue. The exogenous agent may be a peptide or a protein, a nucleic acid, such as an expression construct (e.g., encoding an antisense molecule, a ribozyme, an siRNA, an enzyme, a single-chain antibody, a hormone, a toxin, a tumor suppressor, an inducer of apoptosis, a cell cycle regulator, a cytokine, or a growth factor), an organopharmaceutical, or a metabolite.

Analyzing may comprise secondary ion mass spectrometry, laser desorption mass spectrometry or matrix-assisted laser desorption mass spectrometry, desorption electrospray or electrospray mass spectrometry. The intact tissue may comprises at least a second spatially discrete microregion, and the method further comprises subjecting the second spatially discrete microregion to one or more physical or chemical treatments, and analyzing a sample from the second spatially discrete microregion. The samples from the first and second spatially discrete microregions may be compared. The microregion may be a microwell in the tissue or a tissue plug or cylinder from the tissue. The tissue plug or cylinder may be comprised with an array of tissue plugs or cylinders, each in a spatially discrete relationship to each other.

In yet another embodiment, there is provided a method for analyzing an endogenous metabolite in a tissue comprising (a) providing an intact tissue comprising a first spatially discrete microregion; (b) subjecting the microregion to one or more physical or chemical treatments; and (c) analyzing a endogenous metabolite sample from the microregion, thereby providing analysis of endogenous metabolite content in the tissue. The endogenous metabolite may be an organic acid metabolite, peptide metabolites, or a part of a sugar.

In another embodiment, there is provided a method for analyzing the delivery of an exogenous agent to a tissue comprising (a) providing an intact tissue comprising a first spatially discrete microregions; (b) contacting the tissue with the agent; (c) subjecting at the first spatially discrete microregion to one or more physical or chemical treatments; and (d) analyzing a sample from the first spatially discrete microregion, thereby providing analysis of the delivery of the exogenous agent to the tissue. The exogenous agent may be a peptide or a polypeptide, a nucleic acid, such as an expression construct (e.g., encoding an antisense molecule, a ribozyme, an siRNA, an enzyme, a single-chain antibody, a hormone, a toxin, a tumor suppressor, an inducer of apoptosis, a cell cycle regulator, a cytokine, or a growth factor), an organopharmaceutical, or a metabolite.

Analyzing may comprise secondary ion mass spectrometry, laser desporption mass spectrometry or matrix-assisted laser desporption mass spectrometry, desorption electrospray or electrospray mass spectrometry. The intact tissue may comprise at least a second spatially discrete microregion, and the method further comprises subjecting the second spatially discrete microregion to one or more physical or chemical treatments, and analyzing a sample from the second spatially discrete microregion. The content samples from the first and second spatially discrete microregions may be compared. The exogenous agent is delivered to the tissues as a whole or just to the microregion.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions and kits of the invention can be used to achieve methods of the invention.

Throughout this application, the term "about" is used to indicate that a value includes the inherent variation of error for the device, the method being employed to determine the value, or the variation that exists among the study subjects.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2A, low magnification image of microwells. FIG. 2B, a magnification of the boxed area in FIG. 2A.

FIG. 3A, image with 150 μm magnification. FIG. 3B, image with 75 μm magnification. FIG. 3C, image with 6.67 μm magnification.

FIG. 4A, SEM image taken with a −3 degree tilt. FIG. 4B, SEM image taken with a 0 degree tilt. FIG. 4C, SEM image taken with a +3 degree tilt. FIG. 4D, SEM image taken with a +9 degree tilt.

FIG. 7A, microwells in mouse embryo. FIG. 7B, microwells in human brain.

FIG. 9A, an image of the entire mouse brain is shown. FIG. 9B, a magnification of the top of well A1 in FIG. 9A is shown. Confocal microscopy of a microwell is shown at the depths of 3 μm (FIG. 9C), 4.4 μm (FIG. 9D), 5 μm (FIG. 9E), 6 μm (FIG. 9F), 7 μm (FIG. 9G), and 8 μm (FIG. 9H).

FIG. 11A, MS data indicating the presence of the sequence of the mouse β tubulin protein are indicated with the "*" symbol. FIG. 11B, MS data from fragmentation of the 1619.8 Da peptide. FIG. 11C, MS data from fragmentation of the 1052.6 Da peptide.

FIG. 12A, MS data indicating the presence of the sequence of the sequence of MBP6, AAA39496, M calc 18476 are indicated with the "*" symbol. FIG. 12B, MS data from fragmentation of the 1339.7 Da peptide.

DETAILED DESCRIPTION OF ILLUSTRATIVE EMBODIMENTS

I. The Present Invention

Figure 1:
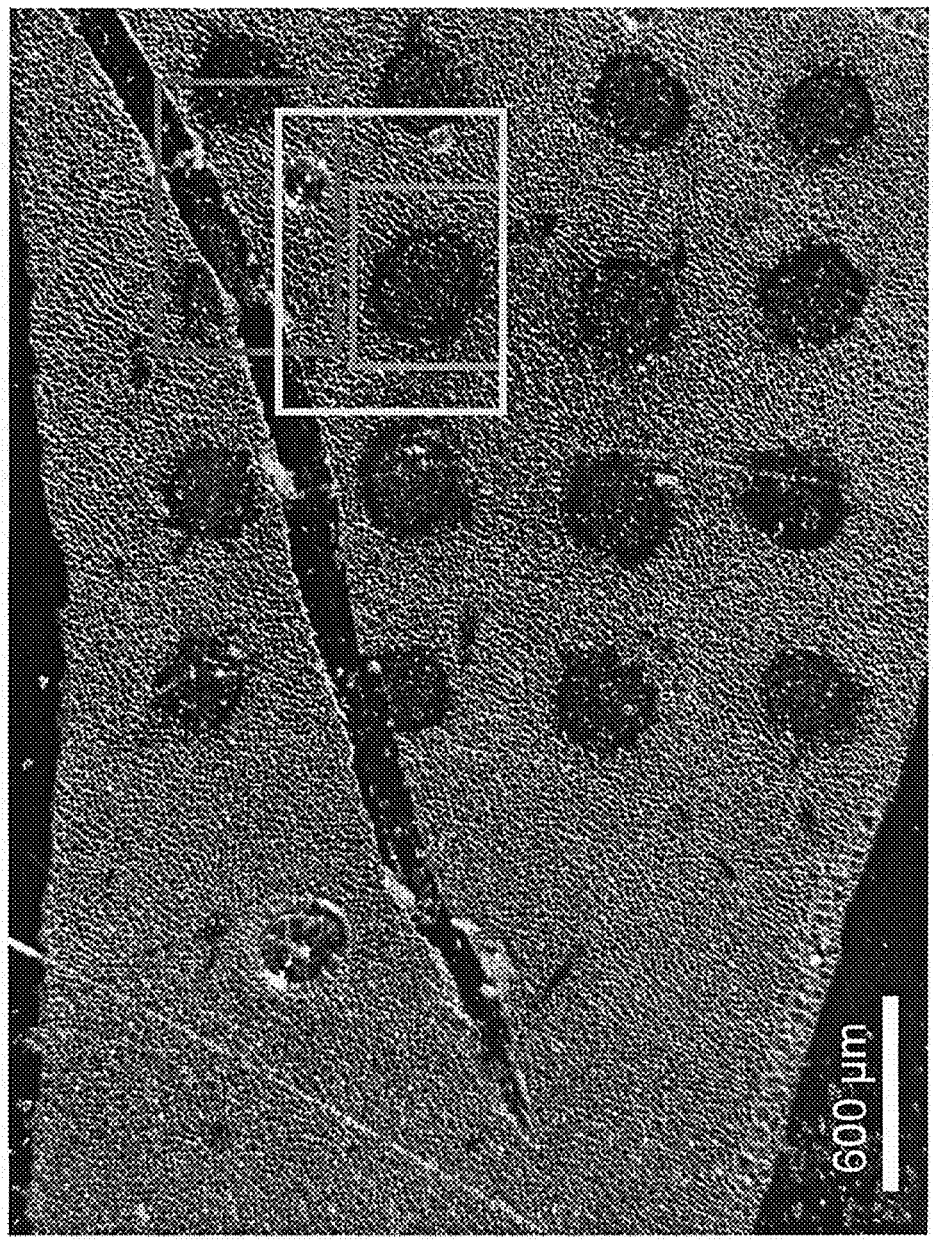
FIG. 1—Image of microwells in rat liver tissue. The image was taken using an optical microscope.

Proteomics is an extremely powerful tool in examining cellular function, and provides a complementary analysis to genomics efforts. While it is somewhat more complicated to examine protein expression profiles, mass spectrometry (MS), because of its extreme selectivity and sensitivity, has now become a favored tool in the global examination of protein expression. However, a limitation on any analysis of this nature is the need to interrogate molecular changes in discrete tissue samples while permitting high throughput.

Traditional methods of examining proteomes with MS involve homogenizing small samples of tissues, using separative techniques such as 2D gels or liquid chromatography, which are followed by MS for detection. Although this method gives adequate results, it is tedious, labor intensive and destroys any spatial fidelity in the sample due to the homogenization proess. Therefore, current approaches to MS quantification of protein expression require substantial improvements in sample processing and utilization.

The present inventors have developed a method for analyzing protein expression in situ, i.e., directly in intact tissues and within discrete areas thereof. In particular embodiments, micron-sized wells are created in intact tissues of interest. The wells create "vessels" in which chemistries can be performed, such as detergent extractions, labeling reactions, etc. Subsequently, the wells can be interrogated with various techniques, particular mass spectroscopy.

The present invention is not limited, however, to proteomics applications. With relative ease, the methods described herein may be advantageously applied to examining the lipid, carbohydrate, nucleic acid, metabolite or even drug content of a tissue. The details of the invention are described in the following pages.

II. Mass Spectrometry

By exploiting the intrinsic properties of mass and charge, mass spectrometry (MS) can resolved and confidently identified a wide variety of complex compounds, including proteins. Traditional quantitative MS has used electrospray ionization (ESI) followed by tandem MS (MS/MS) (Chen et al., 2001; Zhong et al., 2001; Wu et al., 2000) while newer quantitative methods are being developed using matrix assisted laser desorption/ionization (MALDI) followed by time of flight (TOF) MS (Bucknall et al., 2002; Mirgorodskaya et al., 2000; Gobom et al., 2000).

A. ESI

ESI is a convenient ionization technique developed by Fenn and colleagues (Fenn et al., 1989) that is used to produce gaseous ions from highly polar, mostly nonvolatile biomolecules, including lipids. The sample is injected as a liquid at low flow rates (1-10 μL/min) through a capillary tube to which a strong electric field is applied. The field generates additional charges to the liquid at the end of the capillary and produces a fine spray of highly charged droplets that are electrostatically attracted to the mass spectrometer inlet. The evaporation of the solvent from the surface of a droplet as it travels through the desolvation chamber increases its charge density substantially. When this increase exceeds the Rayleigh stability limit, ions are ejected and ready for MS analysis.

A typical conventional ESI source consists of a metal capillary of typically 0.1-0.3 mm in diameter, with a tip held approximately 0.5 to 5 cm (but more usually 1 to 3 cm) away from an electrically grounded circular interface having at its center the sampling orifice, such as described by Kabarle et al. (1993). A potential difference of between 1 to 5 kV (but more typically 2 to 3 kV) is applied to the capillary by power supply to generate a high electrostatic field ($10^6$ to $10^7$ V/m) at the capillary tip. A sample liquid carrying the analyte to be analyzed by the mass spectrometer, is delivered to tip through an internal passage from a suitable source (such as from a chromatograph or directly from a sample solution via a liquid flow controller). By applying pressure to the sample in the capillary, the liquid leaves the capillary tip as a small highly electrically charged droplets and further undergoes desolvation and breakdown to form single or multicharged gas phase ions in the form of an ion beam. The ions are then collected by the grounded (or negatively charged) interface plate and led through an the orifice into an analyzer of the mass spectrometer. During this operation, the voltage applied to the capillary is held constant. Aspects of construction of ESI sources are described, for example, in U.S. Pat. Nos. 5,838,002; 5,788, 166; 5,757,994; RE 35,413; 6,756,586, 5,572,023 and 5,986, 258.

B. ESI/MS/MS

In ESI tandem mass spectroscopy (ESI/MS/MS), one is able to simultaneously analyze both precursor ions and product ions, thereby monitoring a single precursor product reaction and producing (through selective reaction monitoring (SRM)) a signal only when the desired precursor ion is present. When the internal standard is a stable isotope-labeled version of the analyte, this is known as quantification by the stable isotope dilution method. This approach has been used to accurately measure pharmaceuticals (Zweigenbaum et al., 2000; Zweigenbaum et al., 1999) and bioactive peptides (Desiderio et al., 1996; Lovelace et al., 1991). Newer methods are performed on widely available MALDI-TOF instruments, which can resolve a wider mass range and have been used to quantify metabolites, peptides, and proteins. Larger molecules such as peptides can be quantified using unlabeled homologous peptides as long as their chemistry is similar to the analyte peptide (Duncan et al., 1993; Bucknall et al., 2002). Protein quantification has been achieved by quantifying tryptic peptides (Mirgorodskaya et al., 2000). Complex mixtures such as crude extracts can be analyzed, but in some instances sample clean up is required (Nelson et al., 1994; Gobom et al., 2000). Desporption electrospray is a new associated technique for sample surface analysis.

C. SIMS

Secondary ion mass spectroscopy, or SIMS, is an analytical method that uses ionized particles emitted from a surface for mass spectroscopy at a sensitivity of detection of a few parts per billion. The sample surface is bombarded by primary energetic particles, such as electrons, ions (e.g., O, Cs), neutrals or even photons, forcing atomic and molecular particles to be ejected from the surface, a process called sputtering. Since some of these sputtered particles carry a charge, a mass spectrometer can be used to measure their mass and charge. Continued sputtering permits measuring of the exposed elements as material is removed. This in turn permits one to construct elemental depth profiles. Although the majority of secondary ionized particles are electrons, it is the secondary ions which are detected and analysis by the mass spectrometer in this method.

D. LD-MS and LDLPMS

Laser desorption mass spectroscopy (LD-MS) involves the use of a pulsed laser, which induces desorption of sample material from a sample site—effectively, this means vaporization of sample off of the sample substrate. This method is usually only used in conjunction with a mass spectrometer, and can be performed simultaneously with ionization if one uses the right laser radiation wavelength.

When coupled with Time-of-Flight (TOF) measurement, LD-MS is referred to as LDLPMS (Laser Desorption Laser Photoionization Mass Spectroscopy). The LDLPMS method of analysis gives instantaneous volatilization of the sample, and this form of sample fragmentation permits rapid analysis without any wet extraction chemistry. The LDLPMS instrumentation provides a profile of the species present while the retention time is low and the sample size is small. In LDLPMS, an impactor strip is loaded into a vacuum chamber. The pulsed laser is fired upon a certain spot of the sample site, and species present are desorbed and ionized by the laser radiation. This ionization also causes the molecules to break up into smaller fragment-ions. The positive or negative ions made are then accelerated into the flight tube, being detected at the end by a microchannel plate detector. Signal intensity, or peak height, is measured as a function of travel time. The applied voltage and charge of the particular ion determines the kinetic energy, and separation of fragments are due to different size causing different velocity. Each ion mass will thus have a different flight-time to the detector.

One can either form positive ions or negative ions for analysis. Positive ions are made from regular direct photoionization, but negative ion formation require a higher powered laser and a secondary process to gain electrons. Most of the molecules that come off the sample site are neutrals, and thus can attract electrons based on their electron affinity. The negative ion formation process is less efficient than forming just positive ions. The sample constituents will also affect the outlook of a negative ion spectra.

Other advantages with the LDLPMS method include the possibility of constructing the system to give a quiet baseline of the spectra because one can prevent coevolved neutrals from entering the flight tube by operating the instrument in a linear mode. Also, in environmental analysis, the salts in the air and as deposits will not interfere with the laser desorption and ionization. This instrumentation also is very sensitive, known to detect trace levels in natural samples without any prior extraction preparations.

E. MALDI-TOF-MS

Since its inception and commercial availability, the versatility of MALDI-TOF-MS has been demonstrated convincingly by its extensive use for qualitative analysis. For example, MALDI-TOF-MS has been employed for the characterization of synthetic polymers (Marie et al., 2000; Wu et al., 1998). peptide and protein analysis (Zaluzec et al., 1995; Roepstorff et al., 2000; Nguyen et al., 1995), DNA and oligonucleotide sequencing (Miketova et al., 1997; Faulstich et al., 1997; Bentzley et al., 1996), and the characterization of recombinant proteins (Kanazawa et al., 1999; Villanueva et al., 1999). Recently, applications of MALDI-TOF-MS have been extended to include the direct analysis of biological tissues and single cell organisms with the aim of characterizing endogenous peptide and protein constituents (Li et al., 2000; Lynn et al., 1999; Stoeckli et al., 2001; Caprioli et al., 1997; Chaurand et al., 1999; Jespersen et al., 1999).

The properties that make MALDI-TOF-MS a popular qualitative tool—its ability to analyze molecules across an extensive mass range, high sensitivity, minimal sample preparation and rapid analysis times—also make it a potentially useful quantitative tool. MALDI-TOF-MS also enables non-volatile and thermally labile molecules to be analyzed with relative ease. It is therefore prudent to explore the potential of MALDI-TOF-MS for quantitative analysis in clinical settings, for toxicological screenings, as well as for environmental analysis. In addition, the application of MALDI-TOF-MS to the quantification of peptides and proteins is particularly relevant. The ability to quantify intact proteins in biological tissue and fluids presents a particular challenge in the expanding area of proteomics and investigators urgently require methods to accurately measure the absolute quantity of proteins. While there have been reports of quantitative MALDI-TOF-MS applications, there are many problems inherent to the MALDI ionization process that have restricted its widespread use (Kazmaier et al., 1998; Horak et al., 2001; Gobom et al., 2000; Wang et al., 2000; Desiderio et al., 2000). These limitations primarily stem from factors such as the sample/matrix heterogeneity, which are believed to contribute to the large variability in observed signal intensities for analytes, the limited dynamic range due to detector saturation, and difficulties associated with coupling MALDI-TOF-MS to on-line separation techniques such as liquid chromatography. Combined, these factors are thought to compromise the accuracy, precision, and utility with which quantitative determinations can be made.

Because of these difficulties, practical examples of quantitative applications of MALDI-TOF-MS have been limited. Most of the studies to date have focused on the quantification of low mass analytes, in particular, alkaloids or active ingredients in agricultural or food products (Wang et al., 1999; Jiang et al., 2000; Wang et al., 2000; Yang et al., 2000; Wittmann et al., 2001), whereas other studies have demonstrated the potential of MALDI-TOF-MS for the quantification of biologically relevant analytes such as neuropeptides, proteins, antibiotics, or various metabolites in biological tissue or fluid (Muddiman et al., 1996; Nelson et al., 1994; Duncan et al., 1993; Gobom et al., 2000; Wu et al., 1997; Mirgorodskaya et al., 2000). In earlier work it was shown that linear calibration curves could be generated by MALDI-TOF-MS provided that an appropriate internal standard was employed (Duncan et al., 1993). This standard can "correct" for both sample-to-sample and shot-to-shot variability. Stable isotope labeled internal standards (isotopomers) give the best result.

With the marked improvement in resolution available on modern commercial instruments, primarily because of delayed extraction (Bahr et al., 1997; Takach et al., 1997), the opportunity to extend quantitative work to other examples is now possible; not only of low mass analytes, but also biopolymers. Of particular interest is the prospect of absolute multi-component quantification in biological samples (e.g., proteomics applications).

The properties of the matrix material used in the MALDI method are critical. Only a select group of compounds is useful for the selective desorption of proteins and polypeptides. A review of all the matrix materials available for peptides and proteins shows that there are certain characteristics the compounds must share to be analytically useful. Despite its importance, very little is known about what makes a matrix material "successful" for MALDI. The few materials that do work well are used heavily by all MALDI practitioners and new molecules are constantly being evaluated as potential matrix candidates. With a few exceptions, most of the matrix materials used are solid organic acids. Liquid matrices have also been investigated, but are not used routinely.

III. Tissue Microregions

A. Obtaining Tissue Specimens

In accordance with the present invention, intact tissue samples are obtained by standard methodologies. The tissue samples must be of a sufficient size to permit creation of a plurality of microregions, e.g., at least 1 micron to several millimeters, including sizes in between, such as 2 μm, 3 μm, 4 μm, 5 μm, 6 μm, 7 μm, 8 μm, 9 μm, 10 μm, 15 μm, 20 μm, 25 μm, 30 μm, 35 μm, 40 μm, 45 μm, 50 μm, 60 μm, 70 μm, 80 μm, 90 μm, 100 μm, 125 μm, 150 μm, 175 μm, 200 μm, 250 μm, 275 μm, 300 μm, 400 μm, 450 μm, 500 μm, 600 μm, 700 μm, 800 μm, 900 μm, 1000 μm, 2 mm, 3 mm, 4 mm and 5 mm.

Biopsy procedures will generally involve the sterility required of surgical operations, even though the tissues being sample are from cadavers or animals that will be sacrificed. For internal tissues, incisions will be made proximal to the tissue of interest, followed by retraction, excision of tissue and surgical closing of the incision. Superficial tissue sites are accessed by simple excision of the available tissue.

Because tissue viability is an important aspect of the invention, post-surgical treatment requires that tissues be handled such that (a) the integrity of the tissue is maintained and (b) that the cells within the tissue, particularly those in the region (s) where microwells will be created, are not damaged. Appropriate physiologic buffers are generally applied to the tissue, or the tissues are immersed therein. The tissue may also be cooled to appropriate temperatures for limited periods of time. Steps should be taken to ensure that apoptosis or other cellular degradation will not be induced in the tissue specimen.

B. Pretreatment

Pretreatment with of tissues prior to creation microregions may prove advantageous. On particularly useful pretreatment is an ethanol wash, optionally followed by a storage period of minutes to hours. In tests on several tissue types, improved well formation was observed using this approach. Also, the delivery of matrix in a solvent comprising 10% acetonitrile, 60% water, 30% isopropanol and 0.5% acetic acid provided improved results.

C. Microregions

A microregion is an area on the tissue sample that comprise substructure or areas of cellular change or areas of unique interest because of their morphology. The size ranges from nanometers to millimeters.

The microregions can be made chemically or physical. For example, a blunt object can be used to tap into the tissue to form a well or wells, or cut into the tissue to create a well or wells, or to create a microplug or microplugs. Microwells can also be made by laser treatment. Examples of cutting include the use of a capillary tube or an array of capillary tubes to create a spatially fixed group of microplugs that can be transferred to a substrate and, optionally, retained within the capillary array so as to retain structural integrity of the microplug and to prevent contamination of microplugs with adjacent tissue or treatment. Finally, the wells may be created using chemical preparatory treatments described below, i.e., proteases, lipase and the like.

The tissue may be affixed to a support to facilities creation of the microregions, i.e., to provide a stable foundation. Paraffin is one such support, although artificial surfaces such as glass may be utilized.

D. Automation

The process of well creation may be automated using a "microprinting" device that is capable of physically or chemically creating a microregion in repeatable fashion. The device will be able to delivery solvents to multiple locations on a tissue in a predetermined pattern, or to extract tissue "plugs" and transfer them to an appropriate surface, again retaining a predetermined pattern/relationship traceable to their location in the original tissue. In the former case, using multiple drops of a solvent in a single print pass produces more well pronounced microwell structures than single drops. Multipass prints, though also successful when using multiple drops, create larger wells.

IV. Sample Preparation

Once one has obtained and prepared tissues sections containing microwells according to the present invention, it will be necessary to treat the microwells in order to liberate proteins for further analysis. A wide variety of techniques may be applied to the microwells including detergent extraction, treatment with various enzymes (lipases, collagenases, proteases, nucleases) or even with enzyme inhibitors (protease inhibitors). Examples of these treatments are provided below.

A. Detergent Extraction

In order to perform mass spectroscopic or other analysis of protein materials from samples of the present invention, certain treatments are required to prepare the proteins. At a minimum, proteins will be solubilized using detergent extraction. A variety of detergents are available for protein extraction, including anionic, cationic, zwitterionic and non-ionic detergents. By virtue of their amphipathic nature, detergents are able to disrupt bipolar membranes to first free and then solublize proteins bound in the membrane or found inside the target cells.

In selecting a detergent, consideration will be given to the nature of the target protein(s), and the fact that anionic and cationic detergents are likely to have a greater effect on protein structure than zwitterionic or non-ionic detergents. However, non-ionic detergents tend to interfere with charge-bases analyses like mass spectroscopy, and are also suspectible to pH and ionic strength. Zwitterionic detergents provide intermediate properties that, in some respects, are superior to the other three detergent types. Offering the low-denaturing and net-zero charge characteristics of non-ionic detergents, zwitterionics also efficiently disrupt protein aggregation without the accompanying drawbacks. Exemplary anionic detergents include chenodeoxycholic acid, N-lauroylsarconsine sodium salt, lithium dodecyl sulfate, 1-octanesulfonic acid sodium salt, sodium cholate hydrate, sodium deoxycholate, sodium dodecyl sulfate and glycodeoxycholic acid sodium salt. Cationic detergents include cetylpyridinium chloride monohydrate and hexadecyltrimethylammonium bromide. Zwitterionic detergents include CHAPS, CHAPSO, SB3-10 and SB3-12. Non-ionic detergents may be selected from N-decanoyl-N-methylglucamine, digitonin, n-dodecyl β-D-maltoside, octyl α-D-glucopyranoside, Triton X-100, Triton X-114, Tween 20 and Tween 80.

The present inventors have described a method utilizing a novel cleavable detergent, 3-[3-(1,1-bisalkyloxyethyl)pyridin-1-yl]propane-1-sulfonate (PPS). This detergent can be used to extract protein contained within the interior of the cell by disrupting cell membranes. Once the proteins are free from the cell, PPS also assists in protein solubilization by shielding the hydrophobic regions of the newly extracted protein from unfavorable interactions with water. The added advantage of PPS over conventional detergents such as sodium dodecyl sulfate or n-octylglucoside is that the detergent properties that interfere with MALDI mass spectrometry can be eliminated prior to analysis. PPS was found to improve sensitivity in MALDI analyses of both soluble proteins and membrane proteins without degrading spectral quality. The virtues of this strategy were applied to whole cell extracts (Norris et al., 2003).

B. Lipases

To the extent that lipid removal by detergent extraction is incomplete, one my choose to utilize enzymes to further degrade lipid contaminants. Such enzymes are called lipases, almost all of which exhibit the catalytic triad Ser-Asp-His (an exception being geotrichium candidum which has Ser-Glu-His). The areas of the protein predicted to be involved in interfacial activation and conformational change show varying sequences, but a large number possess some sort of flap covering the active site.

Lipases are also characterized by the phenomena of interfacial activation. At very low substrate concentrations in aqueous solution, the enzymes are inactive. When the substrate concentration is high enough to form lipid micelles, the enzyme becomes activated. Though the mechanism in not yet fully understood, it appears that the lipase exists in two (or perhaps more) possible conformations. In one extreme, there is a conformation in which a structural element covers the active site, while at the other extreme, there is a structure in which the active site is exposed, allowing substrate to gain access. The micelle may initiate exposure of the active site.

Lipases have been isolated from a wide variety of mammalian and microbial sources. The mammalian lipases can be split into four groups, the hepatic lingual, gastric and pancreatic lipase and microbial lipases into bacterial and fungal. Very little homology has been found within the known sequences, the most conserved feature being the consensus sequence GxSxG found in the substrate binding site. The above-mentioned catalytic triad (Ser-Asp-His) is also a highly conserved. However, this is common to all esterases, not just lipases, as is the α/βhydrolase fold.

Known lipases include triacylglycerol lipase (triglyceride lipase; tributyrase) phospholipase A2 (phosphatidylcholine 2-acylhydrolase, lecithinase A, phosphatidase, phosphatidolipase) lysophospholipase (lecithinase B, lysolecithinase, phospholipase B) acylglycerol lipase (monoacylglycerol lipase) galactolipase, phospholipase A1, lipoprotein lipase (clearing factor lipase, diglyceride lipase, diacylglycerol lipase) dihydrocoumarin lipase, 2-acetyl-1-alkylglycerophosphocholine esterase (1-alkyl-2-acetylglycerophosphocholine esterase, platelet-activating factor acetylhydrolase, PAF acetylhydrolase, PAF 2-acylhydrolase, LDL-associated phospholipase A2 LDL-PLA(2)), phosphatidylinositol deacylase (phosphatidylinositol phospholipase A2) phospholipase C (lipophosphodiesterase I, Lecithinase C, *Clostridium welchii* α-toxin, *Clostridium oedematiens* β- and γ-toxins) phospholipase D, (lipophosphodiesterase II, lecithinase D, choline phosphatase), phosphoinositide phospholipase C (triphosphoinositide phosphodiesterase, phosphoinositidase C, 1-phosphatidylinositol-4,5-bisphosphate phosphodiesterase, monophosphatidylinositol phosphodiesterase. phosphatidylinositol phospholipase C, PI-PLC, 1-phosphatidyl-D-myo-inositol-4,5-bisphosphate inositoltrisphosphohydrolase), alkylglycerophosphoethanolamine phosphodiesterase. (lysophospholipase D), glycosylphosphatidylinositol phospholipase D (GPI-PLD, glycoprotein phospholipase D, phosphatidylinositol phospholipase D, phosphatidylinositol-specific phospholipase D, phosphatidylinositol-glycan-specific phospholipase D), phosphatidylinositol diacylglycerol-lyase (1-phosphatidylinositol phosphodiesterase, monophosphatidylinositol phosphodiesterase, phosphatidylinositol phospholipase C, 1-phosphatidyl-D-myo-inositol inositolphosphohydrolase (cyclic-phosphate-forming)), glycosylphosphatidylinositol diacylglycerol-lyase ((glycosyl)phosphatidylinositol-specific phospholipase C, GPI-PLC, GPI-specific phospholipase C, VSG-lipase, glycosyl inositol phospholipid anchor-hydrolyzing enzyme, glycosylphosphatidylinositol-phospholipase C, glycosylphosphatidylinositol-specific phospholipase C, variant-surface-glycoprotein phospholipase C).

C. Collagenases

Collagen is he most abundant protein in vertebrates, and occurs in almost very tissue. However, for many applications, is it necessary to remove collagen in order to analyze other proteins in a sample. Moreover, analysis of collagen may be of only limited interest. As a result, methods for the removal of collagen are regularly employed in tissue dissociation.

Collagenases are enzymes that are able to cleave the peptide bonds in triple helical collagen molecules. Collagenases from *Clostridium histolyticum* have been known and studied for decades. Clostridopeptidase and clostripain activities also are associated with some collagenase preparations. Collagenase has been shown effective in isolating intact cells from a variety of tissues including bone, cartilage, thyroid, ovary, uterus, skin, endothelium, neuronal, pancreas, heart, liver and tumors.

D. Nucleic Acid Removal

Elimination of nucleic acids from sample prior to analysis can be achieved by chemical or enzymatic means. Chemical removal involves precipitation methods that employ polyethyleneimine (PEI) or streptomycin sulfate precipitation, followed by centrifugation.

Alternatively, enzymes that specifically degrade DNA and/or RNA may be used to remove these molecules. Benzonase is a genetically engineered endonuclease from *Serratia marcescens*. The protein is a dimer of two 30 kDa subunits. The enzyme degrades all forms of DNA and RNA, including single-stranded, double-stranded, linear and circular molecules, and is effective over a wide range of operating conditions. Some sequence specificity has been identified, with GC-rich regions being preferred. More selective enzymes that degrade DNA (DNases) or RNA (RNases) can be utilized as well.

E. Buffers

Once extracted, buffers will often be utilized to preserve the integrity of protein samples. Buffers are aqueous composed of a weak acid (proton donor) and its conjugate base (proton acceptor). The acid or base is partially neutralized and shows little pH change in response to the addition of stronger acids or bases because of the buffers ability to "absorb" hyrogen ions, which determine pH. The most effective pH range for a buffer is generally one pH unit and is centered around the $pK_a$ of the system.

In choosing an appropriate buffer system, one generally takes into account the following considerations. (1) The $pK_a$ of the buffer should be near the desired midpoint pH of the solution. (2) The capacity of the buffer should fall within one to two pH units above or below the desired pH values. If the pH is expected to drop during the procedure, choose a buffer with a $pK_a$ slightly lower than the midpoint pH. Similarly, if the pH is expected to rise, choose a buffer with a slightly elevated pH. (3) The concentration of the buffer should be adjusted to have enough capacity for the experimental system. (4) The pH of the buffer should be checked at the temperature and concentration which will be used in the experimental system. (5) No more than 50% of the buffer components should be dissociated or neutralized by ionic constituents which are generated within or added to the solution. (6) Buffer materials should not absorb light between the wavelengths of 240-700 nm.

Useful buffers include ADA (Na salt), BES, ethyl glycinate, glycine, PBS, lithium citrate, PIPPS, potassium phosphate (mono- or dibasic), sodium citrate, sodium phosphate, TAPS, Tris base, Tris-HCl, MES, Bis-Tris, PIPES (Na salt), ACES, MOPES, TES, HEPES (Na salt), HEPPS, Tricine, Bicine, CHES, CAPS, MOPSO, DIPSO, HEPPSO, POPSO, AMPSO and CAPSO.

Particularly useful buffers for mass spectrometry are volatile buffers, including ammonium bicarbonate and ammonium acetate.

F. Protease Inhibitors

In order to prevent proteins from being non-specifically degraded following extraction, it may be necessary to include inhibitors of proteases, which are enzymes that hydrolyze peptide bonds. Proteases or peptidases are usually categorized as endopeptidases, which cleave internal bonds, or exopeptides, which remove residues from the termini of protein chains. Alternatively, proteases may be classified by virtue of their target sites, such as serines or cysteines.

The following protease-selective inhibitors are known to be useful in accordance with the present invention: antipain dihydrochloride (papain, trypsin); calpain inhibitor I (calpain I and II); calpain inhibitor II (calpain II and I); chymostatin (chymotrypsin); hirudin (thrombin); TLCK.HCl (trypsin, bromelain, ficin, papain); TPCK (chymotrypsin, bromelain, ficin, papain); and trypsin inhibitor (trypsin). Other inhibitors include APMSF, aprotinin, bestatin, leupeptin, pepstatin, PMSF, and TIMP-2.

G. Proteolysis

In other embodiments, it may be desirable to fragment peptides, albeit in a controlled fashion. There are two basic methods for digesting proteins: enzymatic and chemical methods. Enzymatic digestions are more common. An ideal digestion cuts only at a specific amino acid, but cuts at all occurrences of that amino acid. The number of digestion sites should not produce too many peptides because separation of peptides becomes too difficult. On the other can, too few digestions produces peptides too large for certain kinds of analysis.

The most common digestions are with trypsin and lysine specific proteinases, because these enzymes are reliable, specific and produce a suitable number of peptides. The next most common digestion is at aspartate or glutamate using endoproteinase Glu-C or endoproteinase Asp-N. Chymotrypsin is sometimes used, although it does not have a well defined specificity. Proteinases of broad specificity may generate many peptides, and the peptides may be very short. Of the chemical cleavages, cyanogen bromide is the most common. All the chemical digestions are less efficient than a good enzymatic digest. However they do produce only a few peptides, which can ease any purification problem.

V. Applications

In various aspects of the present invention, tissues may be utilized with or without further treatment. For example, by examining the proteome of various tissues, one can identify subjects that have or are at risk of disease, including infections, cancer, autoimmune disorders, diabetes, or virtually any other condition for which protein aberrations are known. As stated above, the invention may also be applied to the examination of nucleic acids, lipids, carbohydrates, or metabolites.

Alternatively, the tissue may have been treated with one or more agents or environmental factors, and the examination may seek to assess the impact of those agents or factors on the tissue. The agents or factors may be candidate substances and applied as part of a screening assay to determine their suitability at therapeutic agents. Alternatively, the agents or factors may be those found in the environment, and the assay will determine whether the agents have a positive or negative impact on the health or viability of the tissue.

Identification of proteins corresponding to predictive MALDI-TOF signals involves two approaches. First, protein extracts from tissue samples will be fractionated by HPLC, 1D SDS-PAGE or solution phase isoelectric focusing and fractions exhibiting the MALDI-TOF MS signals of interest will be subjected to tryptic digestion and analysis by LC-MS-MS. Peptides and their corresponding proteins of origin are identified from MS-MS spectra with Sequest, which correlates uninterpreted MS-MS spectra with theoretical spectra from database sequences (Eng et al., 1994). Confirmation of the protein identities is based on apparent molecular weight of the MS-MS identified proteins compared to pattern-specific signals detected in the MALDI profiles.

A second identification approach will pair LC-MS-MS analyses with stable isotope tags. Protein extracts from two samples to be compared (e.g., samples that differ in MALDI proteome patterns) are chemically tagged with light and heavy (unlabeled vs. deuterium or $^{13}C$-labeled) reagents, then combined, digested and the tagged peptides are then analyzed by LC-MS-MS. Peptides derived from the two samples are distinguished by pairs of signals in full scan MS separated by the mass difference of the light and heavy isotope tags. Pairs of signals whose intensities deviate from unity represent proteins that were differentially present in the original two samples. MS-MS spectra acquired from these peaks in the same LC-MS-MS analyses allow unambiguous identification of the differentially expressed proteins. The best-known version of this approach uses the thiol-reactive ICAT reagents developed by Gygi and Aebersold (Gygi et al., 1999), although newer, acid-cleavable reagents offer more efficient recovery of tagged peptides and produce higher quality MS-MS spectra for identification (Zhou et al., 2002). N-terminal isotope tagging of tryptic peptides enables identification of proteins that differ in posttranslational modifications rather that protein expression level per se (Mason and Liebler, 2003).

A. Diagnostics

In one aspect, the present invention involves the use of mass spectroscopy to diagnosis or predict conditions or disease states in a subject. Ideally, the use of the present invention permits replicate sampling to ensure accuracy, but also permits testing for multiple targets in descrete but spatially related portions of a tissue. Tissue samples may be obtained using protocols described elsewhere in this document.

Conditions that may be diagnosed according to the present invention include, but are not limited to, cancer, infection, congenital disease, exposure to toxicity, diabetes. Generally, the protein expression of one or more protein targets in the tissue sample will be compared in a standard or known expression level, array or distribution. Alternatively, known healthy tissue may be interrogated in parallel to provide the "normal control" to which the sample is compared.

B. Monitoring

In another embodiment, the present invention permits the monitoring of disease development, disease progression, or the effects of a treatment on a subject. Such an assay will comprise, essentially, the same steps a diagnostic method with the exception that the timing of the examination will be based on (a) a previous negative diagnostic result, (b) a previous positive diagnostic result, or (c) a prior treatment application.

C. Screening

In another aspect, the present invention comprises methods for screening drugs for the ability to modulate protein content of a cell. These assays may comprise random screening of large libraries of candidate substances; alternatively, the assays may be used to focus on particular classes of compounds selected with an eye towards structural attributes that are believed to make them more likely to modulate the expression of a desired target protein or proteins.

To identify a modulator, one generally will determine protein expression in the presence and absence of the candidate substance, a modulator defined as any substance that alters the expression. For example, a method generally comprises:

(a) providing a candidate modulator;
(b) contacting the candidate modulator with a tissue sample;
(c) measuring protein content in the tissue sample of step (b); and
(d) comparing the content in step (c) with the content observed in the absence of the candidate modulator,
wherein a difference between the measured characteristics indicates that said candidate modulator is, indeed, a modulator of the compound, cell or animal.

It will, of course, be understood that all the screening methods of the present invention are useful in themselves notwithstanding the fact that effective candidates may not be found. The invention provides methods for screening for such candidates, not solely methods of finding them. As stated above, the invention may also be applied to the examination of nucleic acids, lipids, carbohydrates, or metabolites.

1. Modulators

As used herein the term "candidate modulator" refers to any molecule that may alter stability or expression of a protein target or set of protein targets. The candidate substance may itself be a protein or fragment thereof, a small molecule, or even a nucleic acid molecule. Using lead compounds to help develop improved compounds is know as "rational drug design" and includes comparisons with know inhibitors and activators. The goal of rational drug design is to produce structural analogs of biologically active modulators. By creating such analogs, it is possible to fashion drugs, which are more active or stable than the natural molecules, which have different and desirable properties.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be peptide, polypeptide, polynucleotide, small molecule inhibitors or any other compounds that may be designed through rational drug design starting from known inhibitors or stimulators.

Other suitable modulators include antisense molecules, ribozymes, and antibodies (including single-chain antibodies). Such compounds are described in greater detail elsewhere in this document. For example, an antisense molecule that bound to a translational or transcriptional start site, or splice junctions, would be putative inhibitor of protein expression.

In addition to the modulating compounds initially identified, the inventors also contemplate that other sterically similar compounds may be formulated to mimic the key portions of the structure of the modulators. Such compounds, which may include peptidomimetics of peptide modulators, may be used in the same manner as the initial modulators.

2. In Situ Assays

In accordance with the present invention, examination of discrete regions of a treated tissue sample may be accomplished. In some embodiments, the tissue as a whole may be treated, either before or after its obtention from an organism. In other embodiments, the individual microwells or regions of the tissue may be treated after sample obtention and preparation. In whole tissue treatments, a benefit will be derived from the ability to perform replicate samples in a homogenous tissue environment. Treatment of subregions following obtention provides the advantage that treatments may be varied across different wells or subregions with the expectation that the underlying material is of equivalent quality and does not vary substantially in its pretreatment state.

D. Assessing Delivery of an Agent

In a distinct embodiment from those discussed above, tissue microregions are examined not for expression of endogenous proteins, but for an exogenous agent that is delivered to the tissue. The endogenous agent may be a protein, a peptide (natural or synthetic), a nucleic acid (DNA, RNA, expression constructs, oligonucleotides, antisense, ribozymes, siRNA), or small molecule organopharmaceuticals.

The assessment may be designed to determine the ability of the agent to be delivered to and persist in a target tissue. In addition, it may be desirable to assess the ability of the agent to create another non-endogenous product, such as a protein expressed from an expression vector, a drug created from a prodrug, or a product created from an enzyme.

VI. EXAMPLES

The following examples are included to further illustrate various aspects of the invention. It should be appreciated by those of skill in the art that the techniques disclosed in the examples which follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Scanning Electron Microscopy (SEM) Analysis of the Structure of Microwells in Rat Liver Tissue Microwells in rat liver tissue were produced by the following method. Rat liver tissue was cut into 12 μm thick sections and thaw mounted to a gold coated MALDI target which was cut in 4 pieces. The tissue was washed 2× for 30 sec in 70% ethanol followed by a 15 sec wash in 100% ethanol. The section was then stored in a vacuum desiccator for 10 minutes. Holes were drilled using the RapidSpotter using the following conditions: start stop mode, 6×5 DPS at a 10 Hz drop ejection rate. The solvent was a mixture of 30% isopropanol, 10% acetonitrile and water to which 0.1% acetic acid was added.

The tissue was stored for 4 days in desiccator, then analyzed by scanning electron microscopy (SEM). A thin layer of a metal was sputtered onto the section immediately prior to the analysis. Tissue was analyzed on a CM-12 Electron microscope from Hitachi. Acceleration voltage was 15 kV and filament current was 10 μA. SEM Images were captured and saved to disc. Adobe Photoshop was used for further image processing which included contras and brightness adjustments.

To investigate the three dimensional structure of a well, a tilt experiment was performed. The sample stage of the SEM instrument was tilted from −3 up to +9 degrees and images were obtained.

Figure 2A:
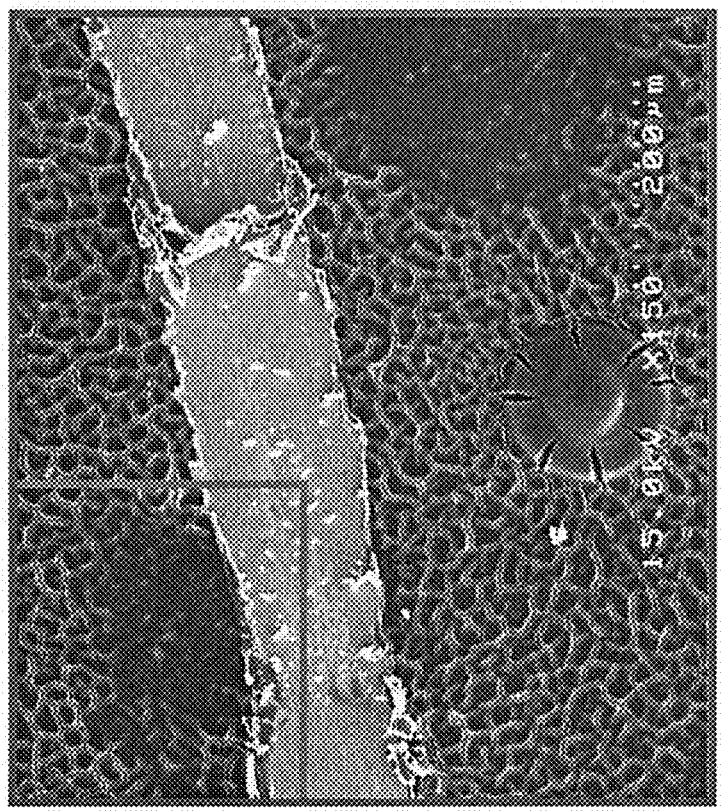
FIGS. 2A-2B—SEM images of microwells in rat liver tissue.
Figure 2B:
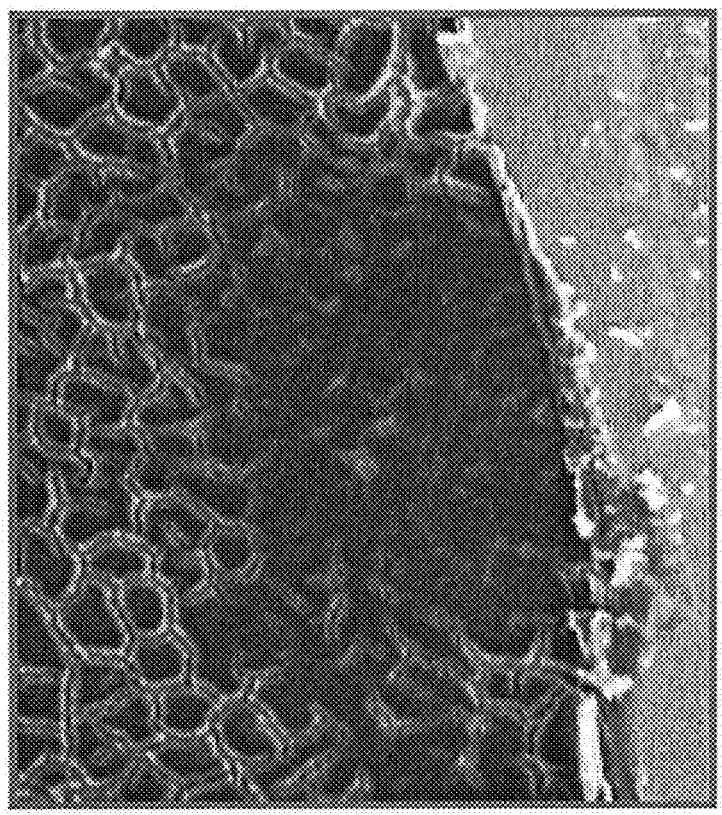
Figure 3A:
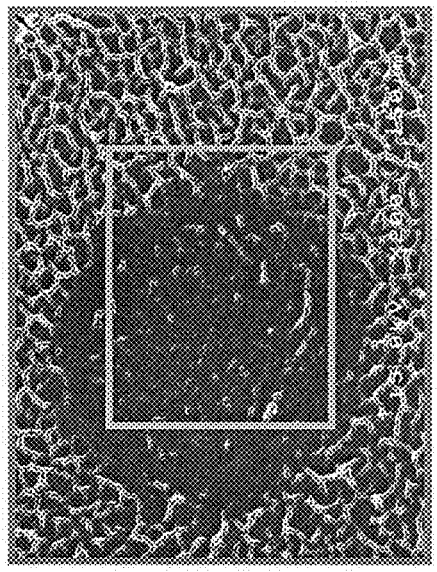
FIGS. 3A-3C—SEM images of microwells in rat liver tissue with increasing magnification.
Figure 3B:
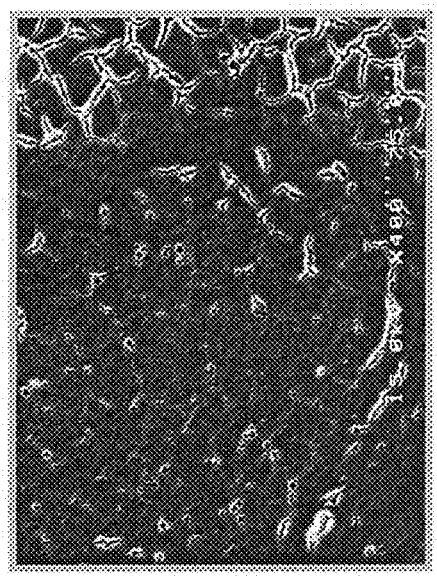
Figure 3C:
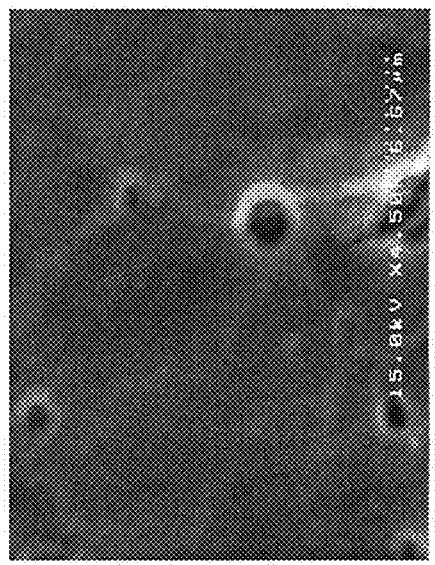
Figure 4B:
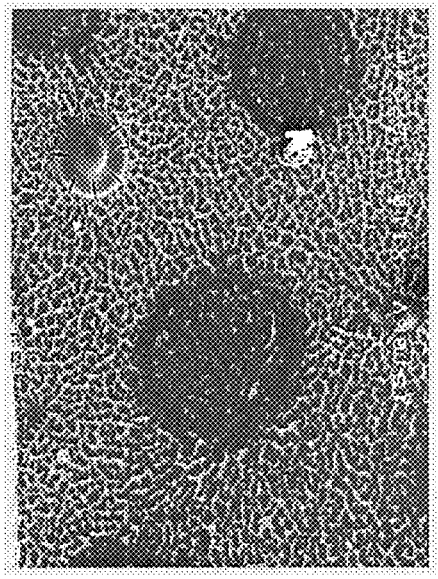
FIGS. 4A-4D—SEM images taken from different angles.
Figure 4D:
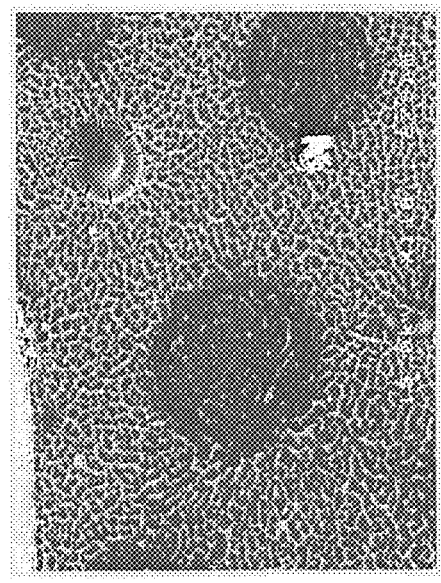
Figure 4A:
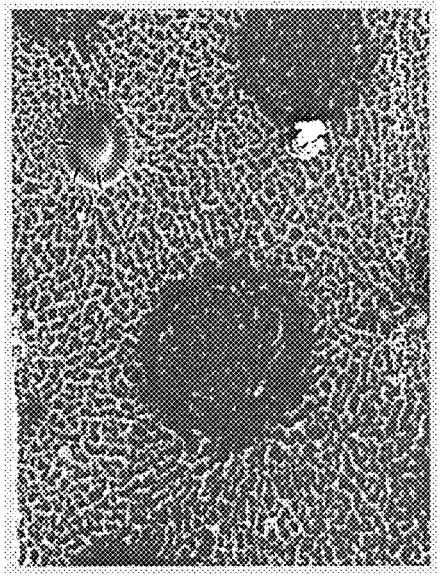
Figure 4C:
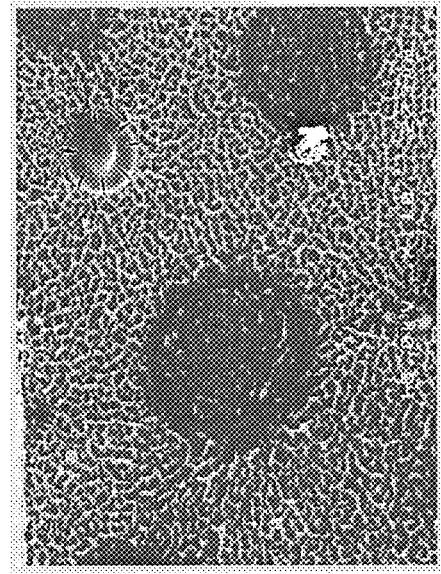

FIG. 1 shows an image of microwells in the rat liver tissue which was subsequently analyzed by SEM. FIG. 2A and FIG. 2B show SEM images of the microwells, and these results indicate that the well evaluated does not reach the bottom of the plate on which the tissue was fixed upon. These results are supported by FIG. 3A, FIG. 3B, and FIG. 3C. SEM images showing images taken from different angles are shown in FIG. 4A, FIG. 4B, FIG. 4C, and FIG. 4D. These results indicate that the microwell structure is particularly well suited for in situ analysis.

Example 2

In Situ Analysis of Microwells

Several aspects of in situ analysis of microwells are evaluated in this example, including: performing in situ reactions in or on tissue, investigating well structures as observed when solvent is applied to the surface of tissue, and performing protein quantification and expression analysis using chemical printing.

Figure 5:
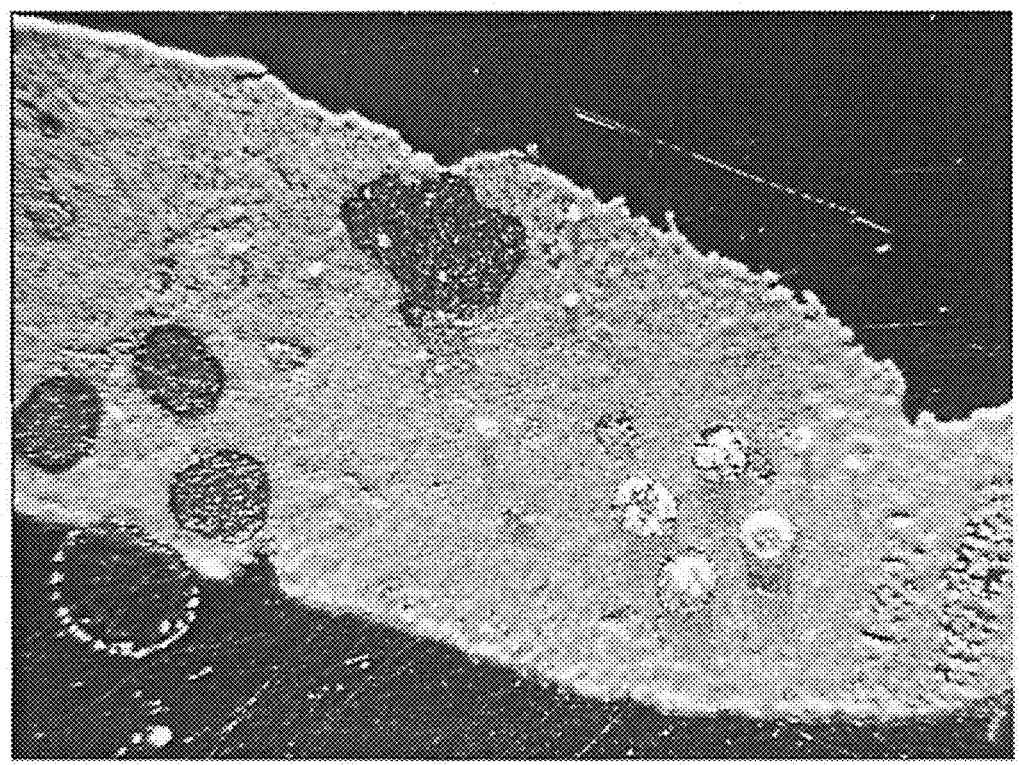
FIG. 5—Microwells in rat liver tissue.

In situ MALDI mass spectroscopy was evaluated on microwells in rat liver tissue. Microwells were generated in rat liver tissue by dispensing a solution on the tissue using the RapidSpotter. FIG. 5 shows spotting of special matrix solution onto washed rat liver tissue. The tissue was washed 2× with 70% Ethanol (30 s each) and 1×15 sec with 100% ethanol. After 2 DPS of a special matrix mix, tissue was gone (FIG. 5). The matrix mix was: saturated solution of sinapinic acid in 30% isopropanol, 10% acetonitrile, 60% $H_2O$ and 0.5% acetic acid. No signals from holes was detected, and the solubility of the matrix was very low. It was observed that the tissue changed aspect during 100% ethanol wash. The results indicate that the tissue dehydrated very well. MALDI spectra obtained after respotting of microwells with 20 mg/ml SA in 50% acetonitrile, 0.1% TFA was extremely good.

Figure 6:
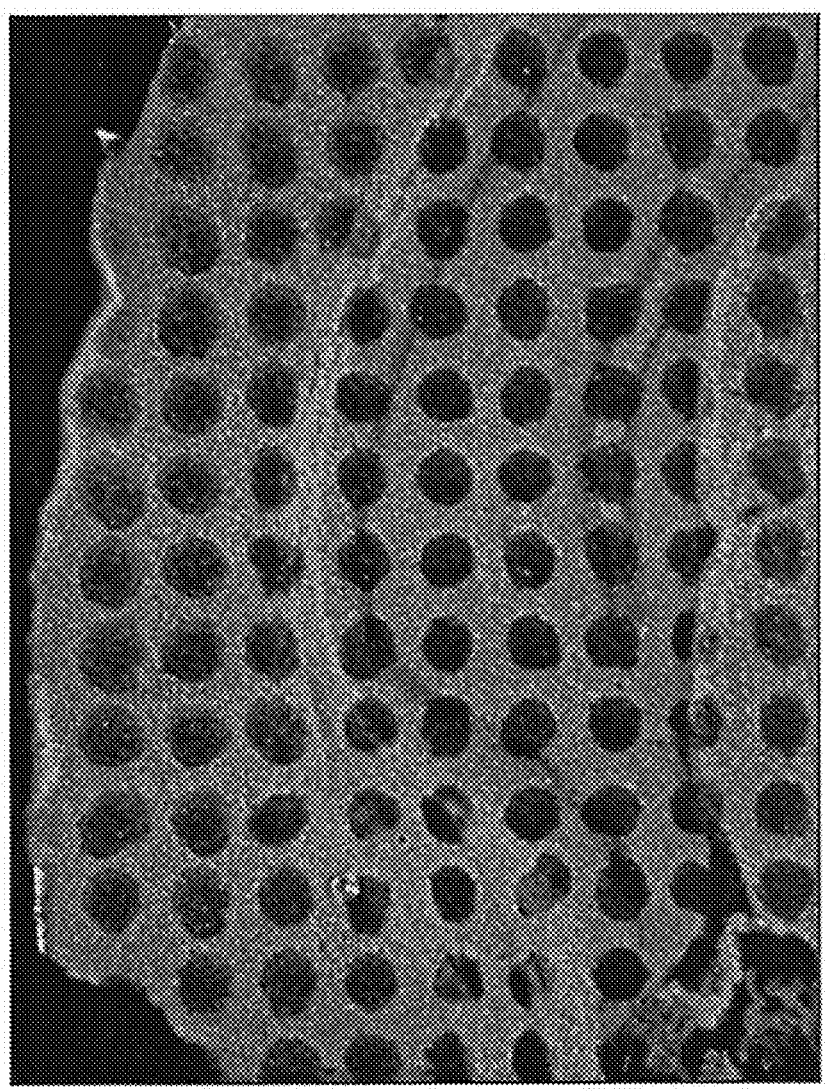
FIG. 6—Microwells in mouse brain tissue.

Microwells were also generated on mouse brain tissue. A 12 μm slice of a mouse brain was ethanol washed with 70% ethanol (2×30 sec) and 100% ethanol (1×15 sec), and the tissue was spotted with 2×3 DPS start stop 10 Hz of a solvent (90% acetonitrile, 0.1% TFA). The results of the spot array generated on the mouse brain tissue is shown in FIG. 6. This procedure of drilling holes into a brain tissue increased the placement accuracy if matrix was dispensed on top of the holes. Interestingly, the microwells form on different regions of the tissue.

Figure 7B:
FIGS. 7A-7B—Images of microwells.
Figure 7A:
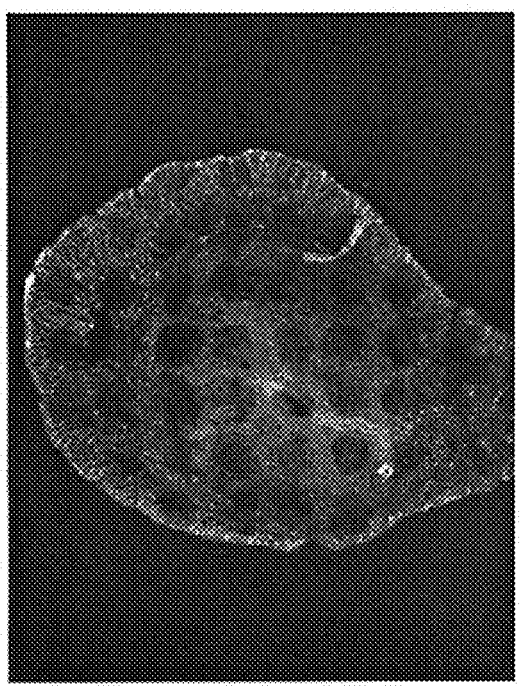
Figure 8B:
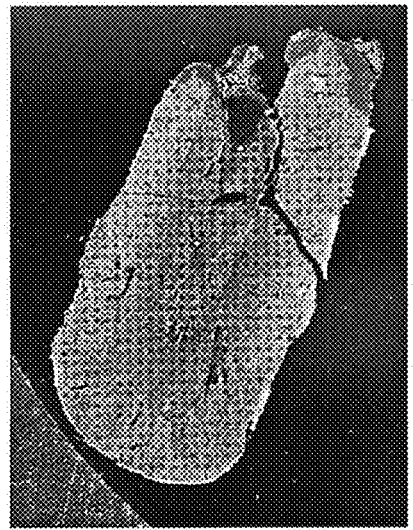
FIGS. 8A-8D—Images of microwells in rat kidney. Microwells were generated by application of 12 μm rat kidney by 1× (FIG. 8A), 2× (FIG. 8B) and 3× (FIG. 8C) 3 DPS 90% acetonitrile, 0.1% TFA spotted. A 3× magnification of the tissue section is shown in FIG. 8D.
Figure 8D:
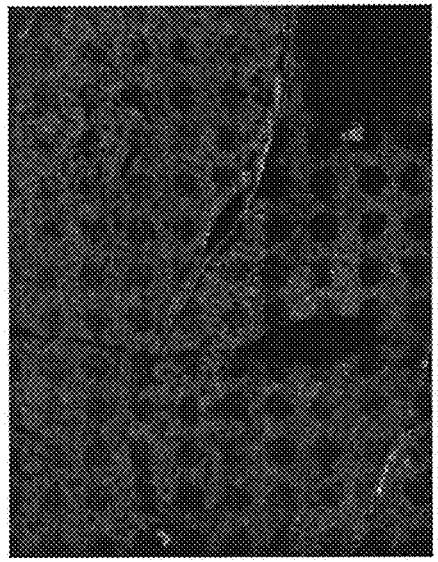
Figure 8A:
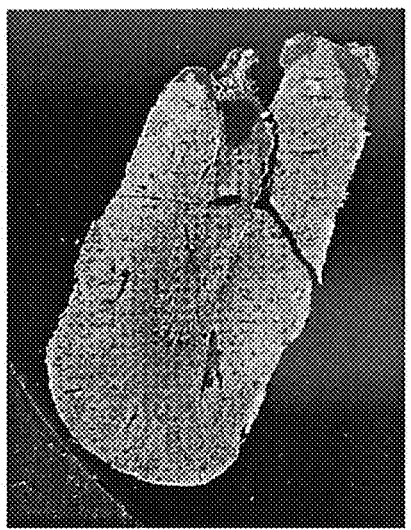
Figure 8C:
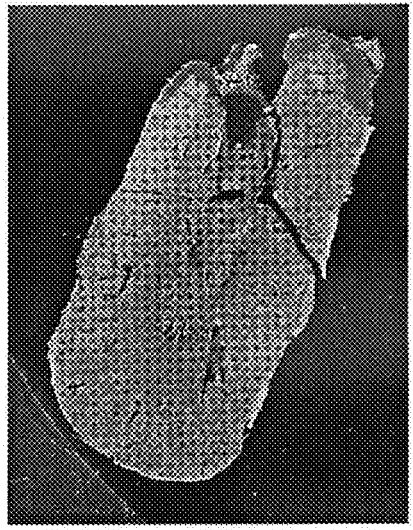
Figure 9B:
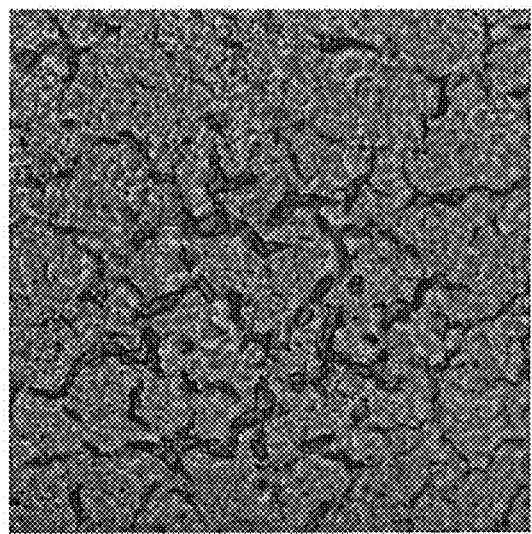
FIGS. 9A-9H—Confocal microscopy of microwells in mouse brain.
Figure 9A:
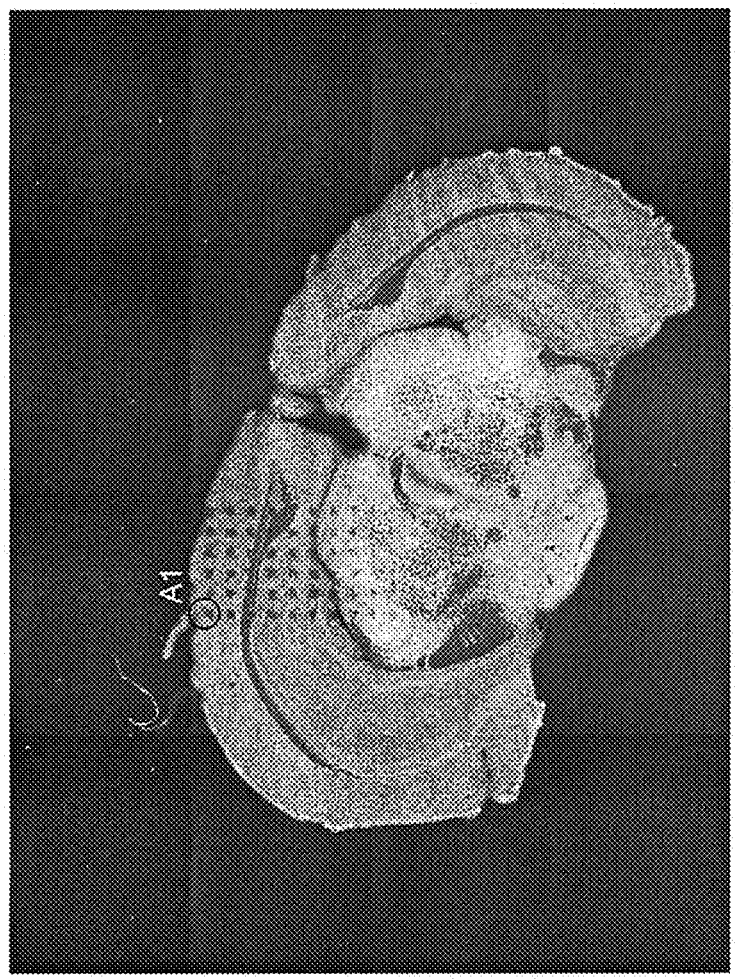
Figure 9C:
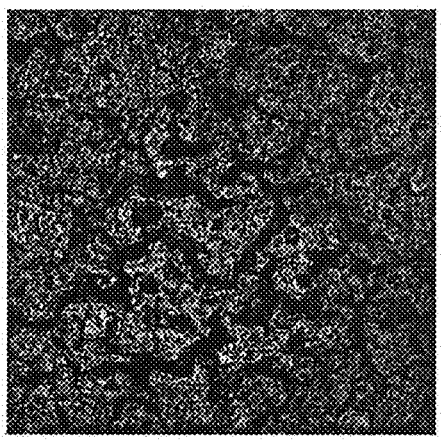
Figure 9D:
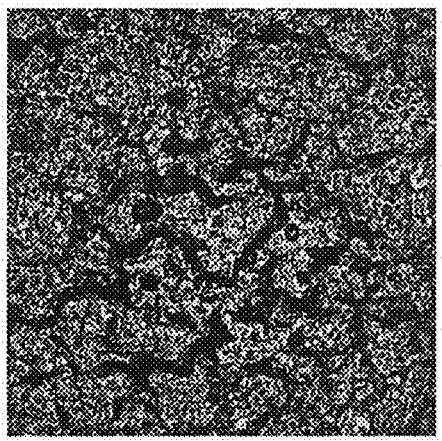
Figure 9E:
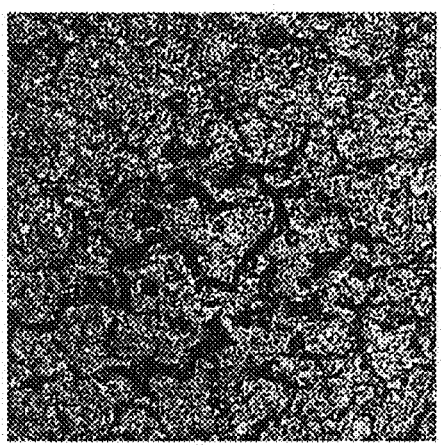
Figure 9F:
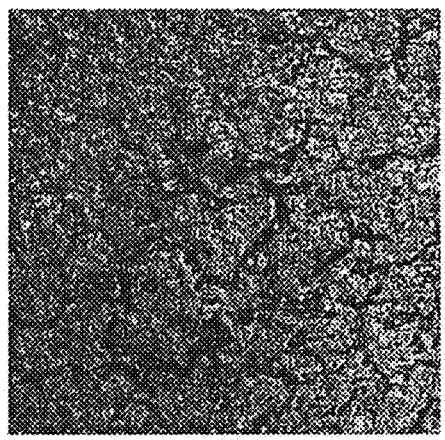
Figure 9G:
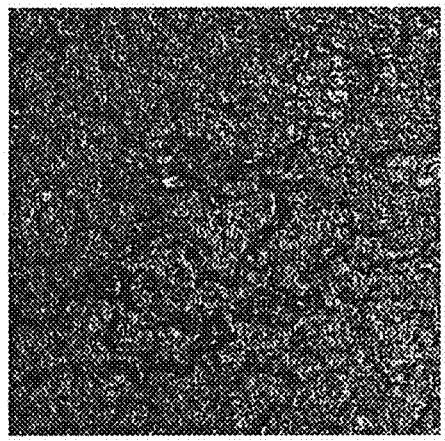
Figure 9H:
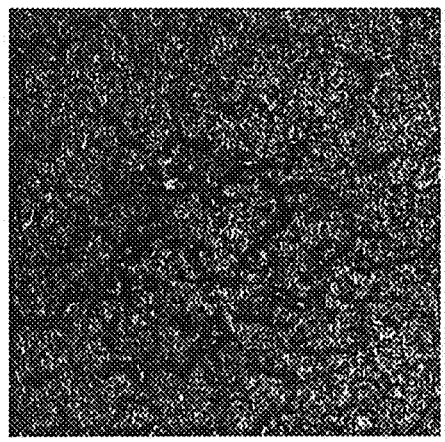

Microwells were generated on different tissues from various species. Microwells were generated on mouse uterus. A 12 μm slice of mouse embryo tissue was ethanol washed with 70% ethanol (2×30 sec) and 100% ethanol (1×15 sec), and the tissue was spotted with 4×2 DPS solvent (90% acetonitrile, 0.1% TFA). These results in the mouse uterus tissue are shown in FIG. 7A. Microwells were also generated on human brain tissue. A 12 μm slice of human brain tissue was spotted with solvent (90% acetonitrile, 0.1% TFA), and the results are indicated in FIG. 7B.

Microwells were also generated on rat kidney tissue. A 12 μm slice of rat kidney was spotted using 1×, 2× and 3×3 DPS 90% acetonitrile, 0.1% TFA. The results of these experiments is shown in FIG. 8A, FIG. 8B, FIG. 8C, and FIG. 8D. These results indicate a good placement accuracy of the matrix which was spotted on the tissue.

Confocal microscopy was used to evaluate the structure of microwells in mouse brain tissue. A 25 μm thick slice of Mouse brain tissue was ethanol washed. Microwells were spotted with 10×3 DPS of 90% acetonitrile, 0.1% TFA. Confocal microscopy images are shown in FIGS. 9A-H. The mouse brain tissue was DIO stained. The laser used was 488 nm. Fluorescence was detected above 505 nm.

Figure 10B:
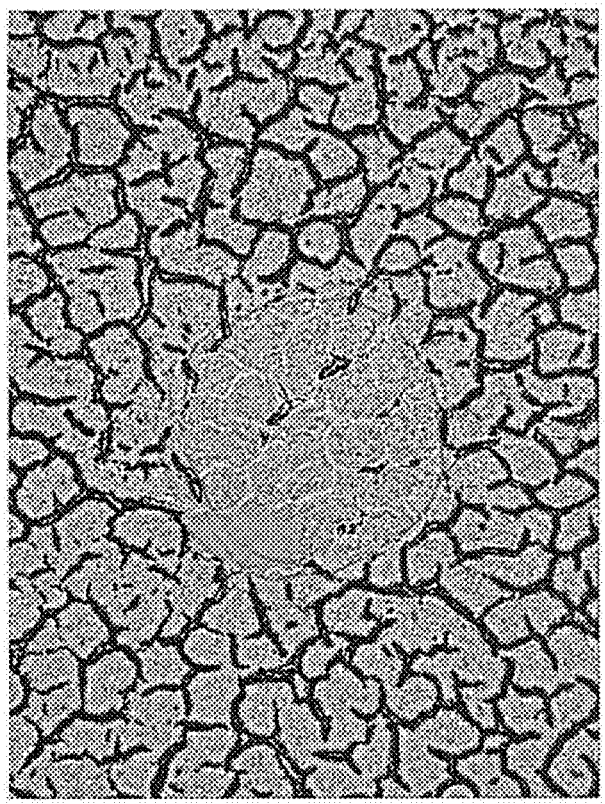
FIGS. 10A-10B—Optical microscopy images. Images of a microwell in rat liver are shown in FIG. 10A and FIG. 10B.
Figure 10A:
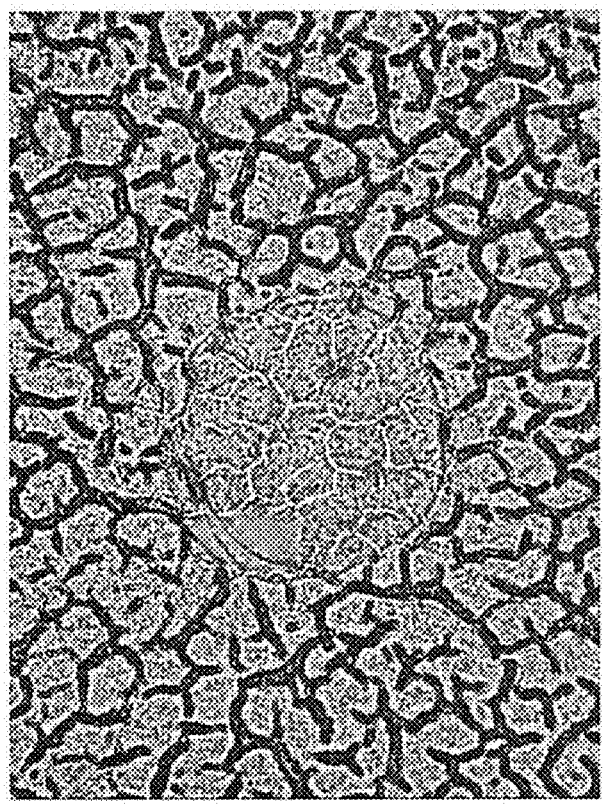

Optical microscopy was performed to evaluate a microwell structure produced in rat liver tissue. Solvent was spotted onto rat liver tissue and optical microscopy images are shown in FIGS. 10A-B. 12 μm slices of rat liver tissue on conductive glass slides are shown. Images were obtained using a microscope 40× magnification. These results indicate that the membrane in this region was completely dissolved.

Figure 11A:
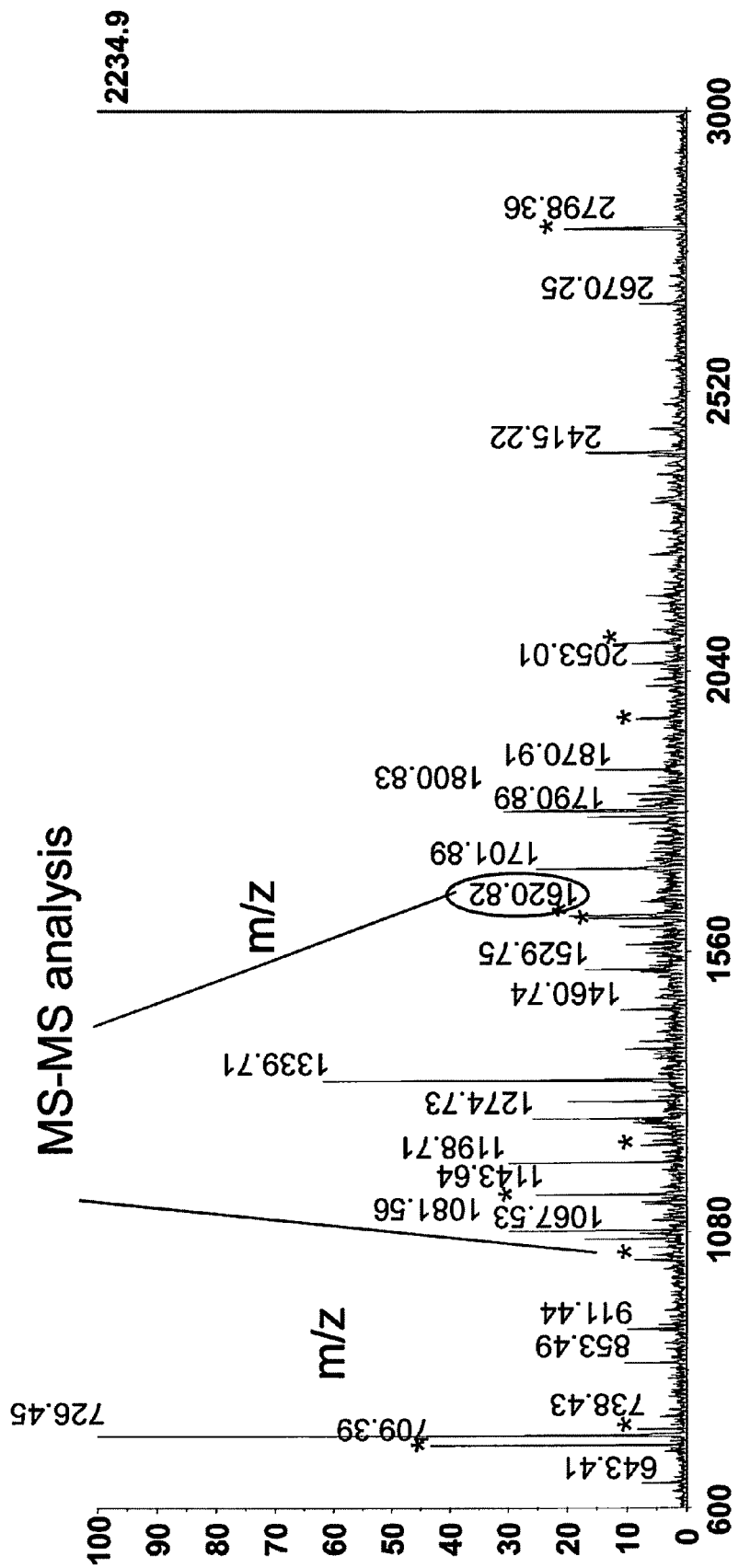
FIGS. 11A-11C—Mass spectroscopy (MS) of microwells generated by tryptic digestion.
Figure 11B:
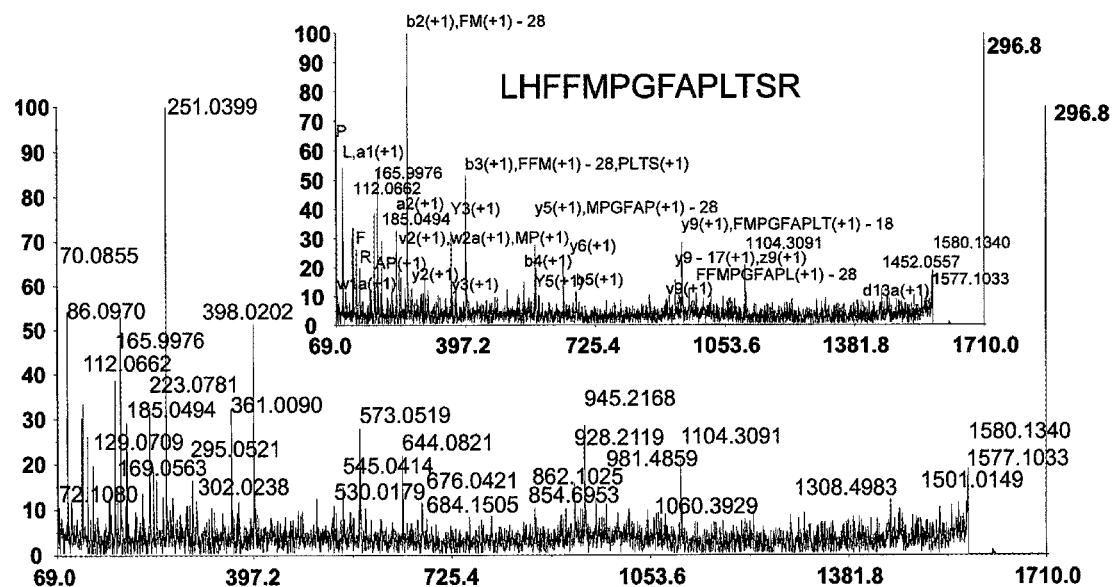
Figure 11C:
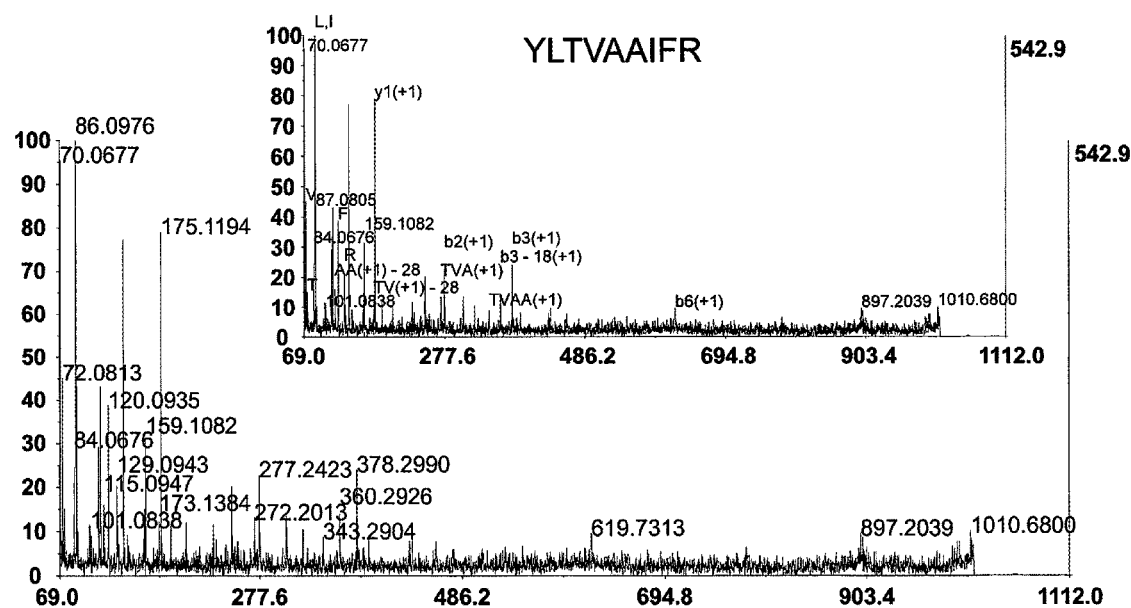
Figure 12A:
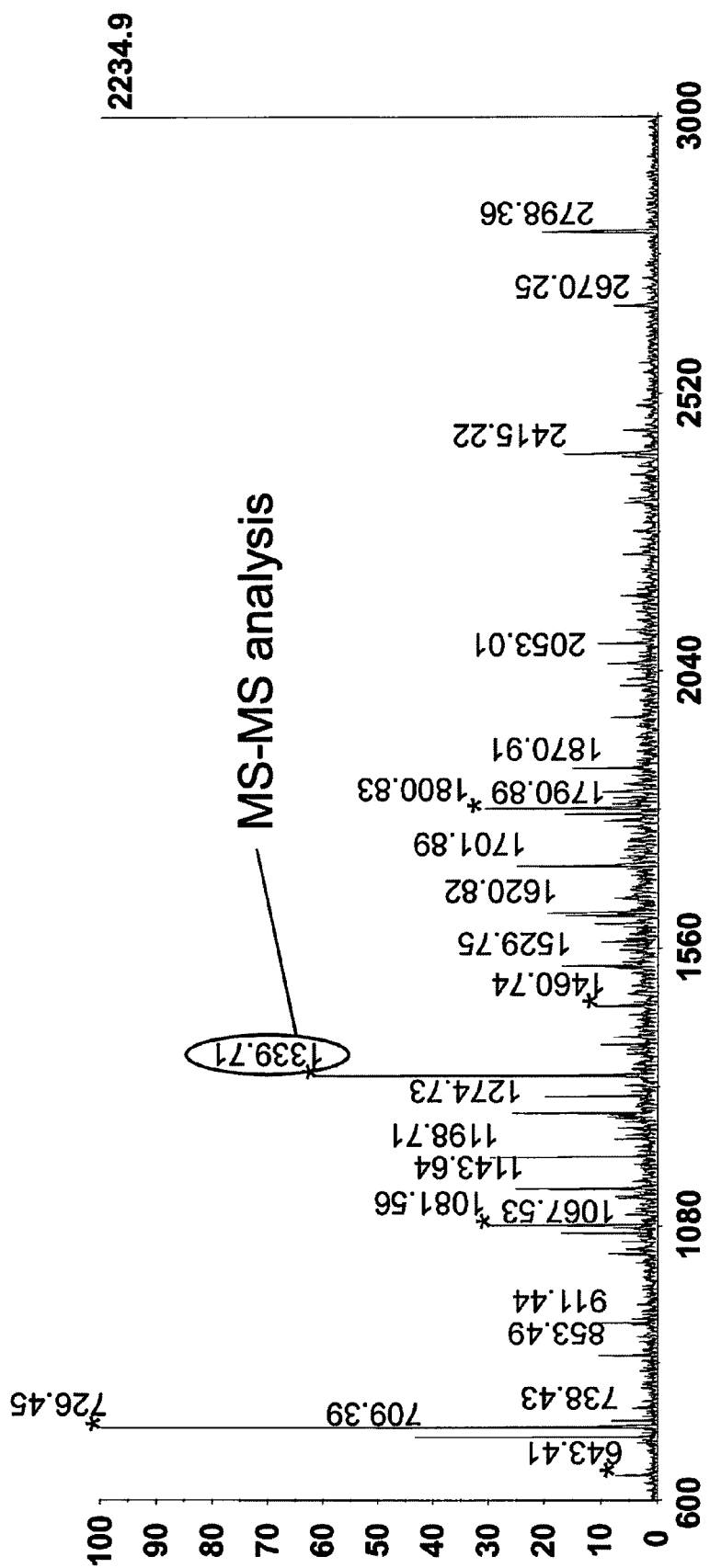
FIGS. 12A-12B—Mass spectroscopy (MS) of microwells generated by tryptic digestion showing identification of the myelin basic protein.
Figure 12B:
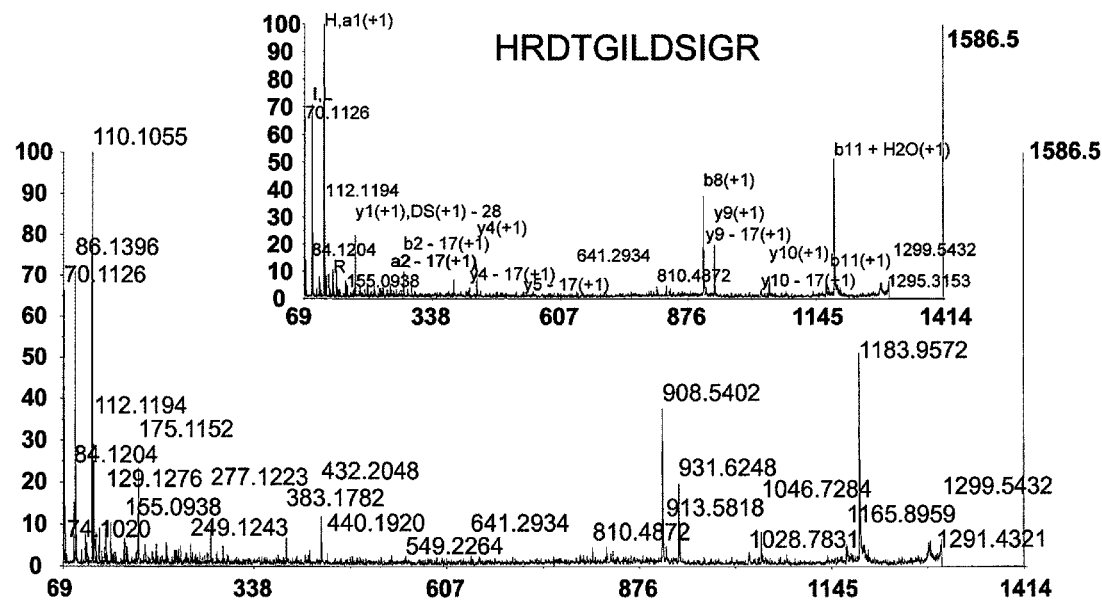

Mass spectroscopy (MS) was performed on a microwell in adult mouse brain tissue. An adult mouse brain was first sectioned on the cryostat (12 μm thickness). The tissue was washed in two consecutive baths of 70% ethanol for 30 sec and 15 sec in 100% ethanol. The washed tissue section was stored in a vacuum desiccator for 1 h. 500 μl of a 10 mmol/l ammonium carbonate buffer solution (pH 8.2, 20° C.) was manually pipetted onto the tissue followed by 500 nl of sequencing grade trypsin prepared at 5 μmol/μl in 2 mmol/l HCl solution. The tissue was then incubated for 30 min at 39° C. in a humidified chamber. The tissue was next allowed to dry on the bench. 500 μl of matrix solution consisting of 10 mg/ml CHCA and 1 mg/ml ammonium citrate (dibasic) in 50% acetonitrile 0.1% TFA was spotted onto each reaction site. Spectra acquisition was obtained with the 4700 proteomics analyzer from Applied Biosystems. FIGS. 11A-C show results indicating the identification of the mouse β tubulin protein Q9CWF2. FIGS. 12A-B indicate the identification of the myelin basic protein. External calibrations were performed using peptide standard mixtures on plates.

Example 3

Ethanol Pretreatment

In order to assess the impact of pretreatments of microwell formation, ethanol washes were performed on cell sections prior to creation of microwells. Tissues were 12 µm thick rat liver on conductive glass slides. The tissues were washed 2× for 30 secs in 70% ethanol followed by 1 wash for 15 secs in reagent grade ethanol. The tissue was stored overnight in a dessicator. Good well formation was observed.

In a second experiment, three different pretreatments were performed on rat liver sections: (a) ethanol wash followed by 130 min in vacuum dessicator; (b) ethanol wash followed by 22 min in vacuum dessicator; (c) no wash followed by 180 min in vacuum dessicator. Again, the ethanol washed tissue gave better results, as did the longer storage samples.

A third experiment using mouse brain tissue, again 12 µm in thickness, was performed. The cryosectioned tissue was thaw mounted on a conductive glass slide and either washed in ethanol or not washed. Solvent (90% acetonitrile containing 0.1% TFA) was spotted at 10 Hz ejection frequency. While holes were produced in both tissues, ethanol washing improved hole formation. There was no visible difference between holes formed at 3×3 and 3×6 DPS.

Example 4

Preparation of Wells Using Solvents and Seeding

In order to assess the performance of various solvents, five different formulations were tested: (a) 30% isopropanol, 10% acetonitrile, 0.5% acetic acid, 60% water; (b) 20% water, 20% acetic acid, 60% isopropanol; (c) 50% acetonitrile, 0.1% TFA; (d) water; and (e) 860 µm Triton x-100 (CMC is 300 µM), 0.15 M NaCl, in 50 mM Tris/HCl buffer pH=7.45 (20° C.). Solvent 1 improved MALDI signals in the low molecular weight range, Solvent 2 seemed to lyse effeciently but the MALDI spectrum showed mainly hemoglobin and Solvent 5 also was dominated by hemoglobin peaks.

Another approach to preparing wells involves use of a seeding material to initiate and homogenize crystal formation. Ethanol washed rat liver was spotted with 200 nl of a saturated sinapinic acid solution in a solvent mixture (10% acetonitrile, 60% water, 30% isopropanol, 0.5% acetic acid) followed by 200 nl of sinapinic acid prepared at 25 mg/ml in 50% acetonitrile containing 0.1% TFA. MALDI crystals were visible in the well.

Example 5

Number of Droplets Versus Number of Print Passes

Figure 13:
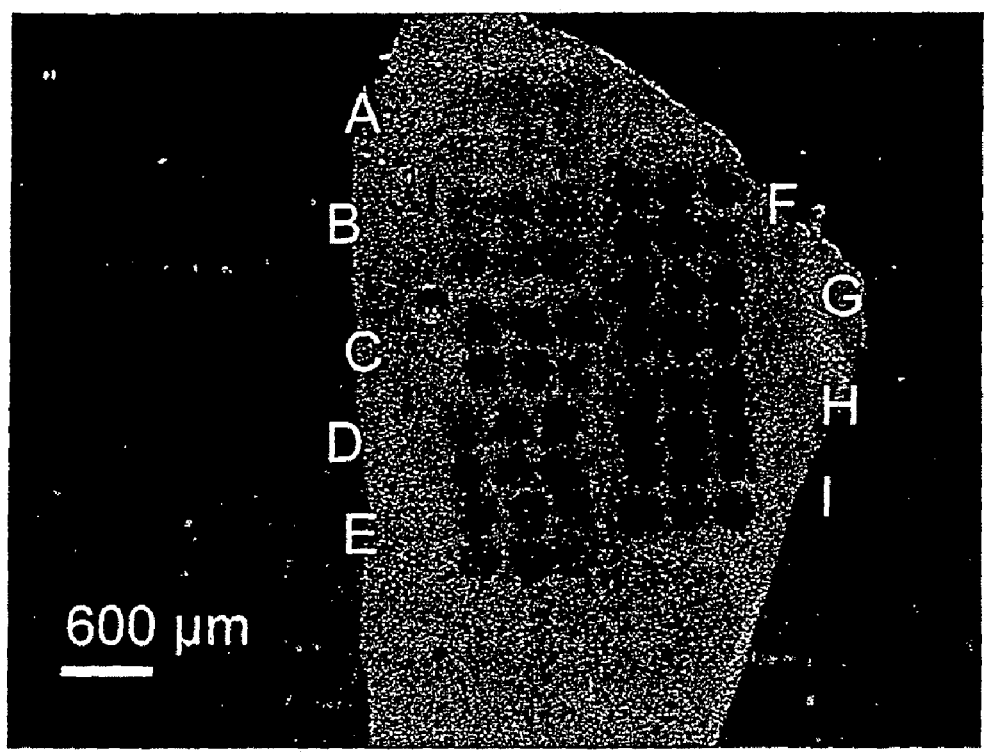
FIG. 13—Microwell formation based on one pass with varying droplet number. Ethanol washed rat liver (12 μm) is spotted with 1-9 droplets (start/stop mode) of the following solvent: 0.5% acetic acid mixed to a solvent mixture of 30% isopropanol, 10% acetonitrile and 60% water. Droplets deposited A) 1 DPS, B) 2 DPS, C) 3 DPS, D) 4 DPS, E) 5 DPS, F) 6 DPS, G) 7 DPS, H) 8 DPS, I) 9 DPS FIGS. 14A-C—Microwell formation based on multiple pass versus multiple droplets.

To assess the impact of multiple droplets on well formation, the following experiment was set up on 12 µm rat liver sections. Ethanol washed tissue was spotted with 1-9 droplets (start/stop mode) of the following solvent: 0.5% acetic acid mixed to a solvent mixture of 30% isopropanol, 10% acetonitrile and 60% water. Droplets deposited A) 1 DPS, B) 2 DPS, C) 3 DPS, D) 4 DPS, E) 5 DPS, F) 6 DPS, G) 7 DPS, H) 8 DPS, I) 9 DPS. As show in FIG. 13, the more droplets used, the more pronounced the wells.

Figure 14A:
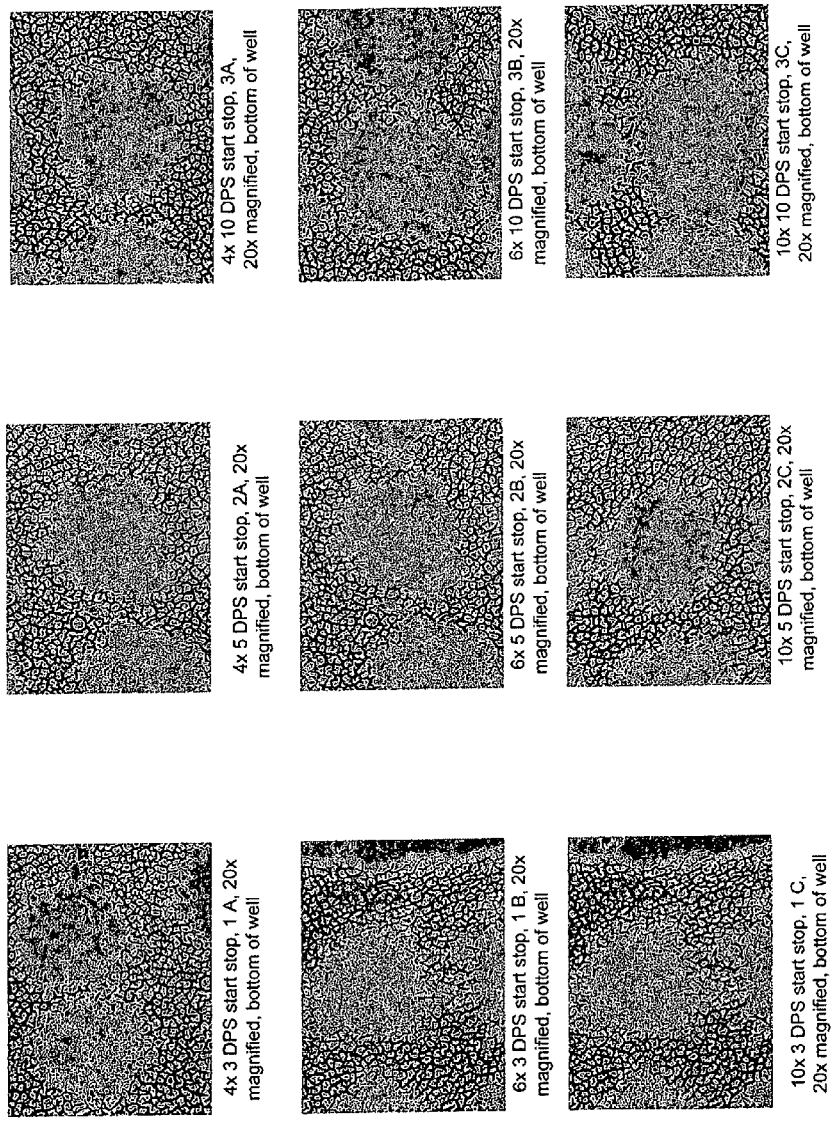
(FIG. 14A) Magnified microwells, no stain.
Figure 14B:
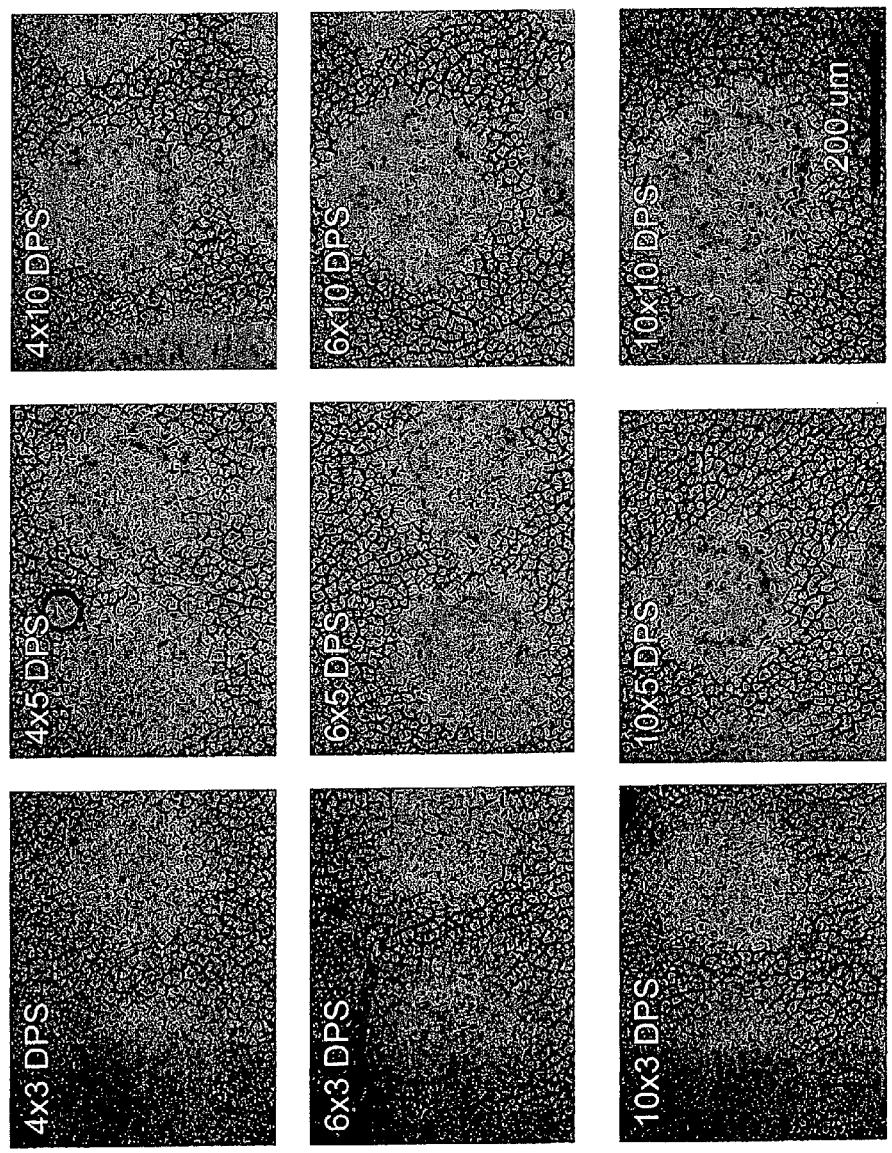
(FIG. 14B) Magnified microwells, stained.
Figure 14C:
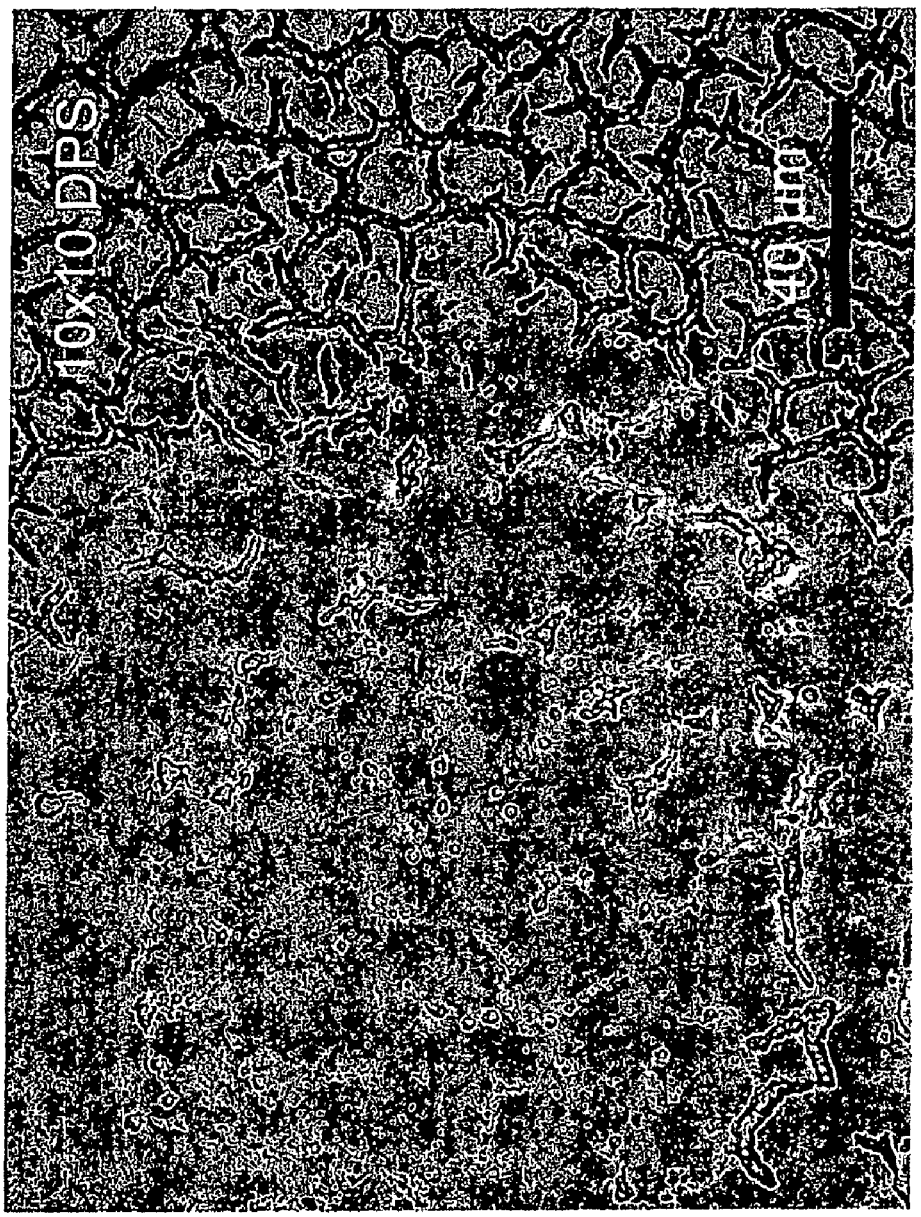
(FIG. 14C) Close up (40×) of methylene blue stained microwell formed in 12 μm rat liver (solvent was 0.5% acetic acid, 30% isopropanol, 10% acetonitrile, 60% water). For FIGS. 14A-B, top row=4 passes, middle row=6 passes, bottom row=10 passes, left column=3 DPS, middle column=4 DPS, right column=5 DPS.

To assess the effects of multiple print passes, rat liver 12 µm was assessed using 4, 6 or 10 passes (A is 4 times, B is 6 times, C is 10 times) and 1) 3 DPS start stop, 2) 5 DPS start stop, or 3) 10 DPS start stop. The solvent was 0.5% acetic acid mixed to a solvent mixture of 30% isopropanol, 10% acetonitrile and 60% water. As show in FIGS. 14A-B, again, more droplets give better wells, and the wells increase in size with passes. FIG. 14C shows a close-up of a stained well.

* * * * * * * * * * *

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VIII. References

The following references, to the extent that they provide exemplary procedural or other details supplementary to those set forth herein, are specifically incorporated herein by reference:

U.S. Pat. No. 5,838,002
U.S. Pat. No. 5,788,166
U.S. Pat. No. 5,757,994
U.S. Pat. RE 35,413
U.S. Pat. No. 6,756,586
U.S. Pat. No. 5,572,023
U.S. Pat. No. 5,986,258
Bahr et al., *J. Mass. Spectrom.*, 32:1111, 1997.
Bentzley et al., *Anal. Chem.*, 68:2141, 1996.
Bucknall et al., *J. Am. Soc. Mass Spectrometry*, 13(9):1015-27, 2002.
Caprioli et al., *Anal. Chem.*, 69:4751, 1997.
Chaurand et al., *Anal. Chem.*, 71:5263, 1999.
Chen et al., *J. Chromatogr. B. Biomed. Sci. Appl.*, 755, 2000.
Desiderio et al., *Biopolymers*, 40:257, 1996.
Duncan et al., *Rapid Commun. Mass Spectrom.*, 7:1090, 1993.
Eng et al., *J. Amer. Soc. Mass Spectrometry*, 5:976-989, 1994.
Faulstich et al., *Anal. Chem.*, 69:4349, 1997.
Fenn et al., *Science*, 246(4926):64-71, 1989.
Gobom et al., *Anal. Chem.* 72:3320, 2000.
Gygi et al., *Mol. Cell. Biol.*, 19:1720, 1999.
Gygi et al., *Nat. Biotechnol.*, 17:994-999, 1999.
Horak et al., *Rapid Commun. Mass Spectrom.*, 15:241, 2001.
Jespersen et al., *Anal. Chem.*, 71:660, 1999.
Jiang et al., *J. Agric. Food Chem.*, 48:3305, 2000.
Kabarle et al., *Anal. Chem.* 65(20):972A-986A, 1993.
Kanazawa et al., *Biol. Pharm. Bull.*, 22:339, 1999.
Kazmaier et al., *Fres. J. Anal. Chem.*, 361:473, 1998.
Li et al., *Trends Biotechnol.*, 18:151, 2000.
Lovelace et al., *J. Chromatogr.*, 562:573, 1991.
Lynn et al., *Rapid Commun. Mass Spectrom.*, 13:2022, 1999.
Marie et al., *Anal. Chem.*, 72:5106, 2000.
Mason and Liebler, *J. Proteome Res.*, 2(3):265-272, 2003.
Miketova et al., *Mol. Biotechnol.*, 8:249, 1997.
Mirgorodskaya et al., *Rapid Commun. Mass Spectrom.*, 14:1226, 2000.
Muddiman et al., *Fres. J. Anal. Chem.*, 354:103, 1996.
Nelson et al., *Anal. Chem.*, 66:1408, 1994.
Nguyen et al., *J. Chromatogr.*, 705:21, 1995.

Norris et al., *Anal Chem.*, 75(23):6642-6647, 2003
Roepstorff et al., *Exs.*, 88:81, 2000.
Stoeckli et al., *Nat. Med.*, 7:493, 2001.
Takach et al., *J. Protein Chem.*, 16:363, 1997.
Villanueva et al., *Enzyme Microb. Technol.*, 29:99, 2001.
Wang et al., *J. Agric. Food. Chem.*, 47:1549, 1999.
Wang et al., *J. Agric. Food. Chem.*, 47:2009, 1999.
Wang et al., *J. Agric. Food. Chem.*, 48:2807, 2000.
Wang et al., *J. Agric. Food. Chem.*, 48:3330, 2000.
Wittmann et al., *Biotechnol. Bioeng.*, 72:642, 2001.
Wu et al., *J. Exp. Med.*, 185:1681-1691, 1997.
Wu et al., *Anal. Chem.*, 70:456 A, 1998.
Wu et al., *Anal. Chem.*, 72:61, 2000.
Yang et al., *J. Agric. Food. Chem.*, 48:3990, 2000.
Zaluzec et al., *Protein Expr. Purif.*, 6:109, 1995.
Zhong et al., *Clin. Chem. ACTA.*, 313:147, 2001.
Zhou et al., *Nat. Biotechnol.*, 20:512-515, 2002.
Zweigenbaum et al., *Anal. Chem.*, 71:2294, 1999.
Zweigenbaum et al., *Anal. Chem.*, 74:2446, 2000.

What is claimed is:

1. A method for analyzing the delivery of an exogenous agent to a tissue comprising:
   (a) providing an intact tissue comprising a first spatially discrete microwell;
   (b) contacting said tissue with said exogenous agent;
   (c) subjecting at said first spatially discrete microwell to one or more physical or chemical treatments; and
   (d) using mass spectrometry to a sample from said first spatially discrete microwell, thereby providing analysis of the delivery of said exogenous agent to said tissue, wherein said exogenous agent is a peptide, a polypeptide, a nucleic acid, an organopharmaceutical or a metabolite.

2. The method of claim 1, wherein said nucleic acid is an expression construct.

3. The method of claim 2, wherein said expression construct encodes an antisense molecule, a ribozyme, an siRNA, an enzyme, a single-chain antibody, a hormone, a toxin, a tumor suppressor, an inducer of apoptosis, a cell cycle regulator, a cytokine, or a growth factor.

4. The method of claim 1, wherein mass spectrometry comprises secondary ion mass spectrometry, laser desorption mass spectrometry or matrix-assisted laser desorption mass spectrometry, desorption electrospray or electrospray mass spectrometry.

5. The method of claim 1, wherein said intact tissue comprises at least a second spatially discrete microwell, and said method further comprises subjecting said second spatially discrete microwell to one or more physical or chemical treatments, and analyzing a sample from said second spatially discrete microwell.

6. The method of claim 5, wherein the samples from said first and second spatially discrete microwell are compared.

7. The method of claim 1, wherein the exogenous agent is delivered to the tissue as a whole.

8. The method of claim 1, wherein the exogenous agent is delivered to the microwell.

* * * * *